(12) United States Patent
Caiazza

(10) Patent No.: US 10,633,454 B2
(45) Date of Patent: *Apr. 28, 2020

(54) EXPRESSION OF MODIFIED GLYCOPROTEINS AND GLYCOPEPTIDES

(71) Applicant: Conagen Inc., Bedford, MA (US)

(72) Inventor: Nicky C. Caiazza, Rancho Santa Fe, CA (US)

(73) Assignee: Conagen Inc., Bedford, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/967,202

(22) Filed: Apr. 30, 2018

(65) Prior Publication Data

US 2018/0251569 A1 Sep. 6, 2018

Related U.S. Application Data

(63) Continuation-in-part of application No. 15/799,785, filed on Oct. 31, 2017, now Pat. No. 10,457,970.

(60) Provisional application No. 62/416,086, filed on Nov. 1, 2016.

(51) Int. Cl.
| | |
|---|---|
| C12N 1/00 | (2006.01) |
| C12N 9/24 | (2006.01) |
| C12N 15/79 | (2006.01) |
| C12P 21/00 | (2006.01) |
| C07K 16/32 | (2006.01) |
| C12N 9/10 | (2006.01) |
| C07K 16/00 | (2006.01) |

(52) U.S. Cl.
CPC .............. *C07K 16/32* (2013.01); *C07K 16/00* (2013.01); *C12N 9/1051* (2013.01); *C12N 15/79* (2013.01); *C12Y 204/01258* (2013.01); C07K 2317/14 (2013.01); C07K 2317/24 (2013.01); C07K 2317/41 (2013.01)

(58) Field of Classification Search
CPC .............................. C07K 14/705; C12N 15/79
See application file for complete search history.

(56) References Cited

U.S. PATENT DOCUMENTS

| | | |
|---|---|---|
| 7,001,772 B2 | 2/2006 | Roessler et al. |
| 7,211,418 B2 | 5/2007 | Metz et al. |
| 7,217,856 B2 | 5/2007 | Weaver et al. |
| 7,635,472 B2 | 12/2009 | Kufer |
| 7,759,097 B2 | 7/2010 | Ono et al. |
| 7,851,191 B2 | 12/2010 | Roessler et al. |
| 7,888,123 B2 | 2/2011 | Ono et al. |
| 8,003,772 B2 | 8/2011 | Weaver et al. |
| 8,026,083 B2 | 9/2011 | Nico Luc et al. |
| 8,206,984 B2 | 6/2012 | Roessler et al. |
| 8,409,825 B2 | 4/2013 | Chiba et al. |
| 8,697,359 B1 | 4/2014 | Zhang |
| 8,883,993 B2 | 11/2014 | Schneider et al. |
| 9,428,784 B2 | 8/2016 | Choi et al. |
| 9,932,599 B2 | 4/2018 | Caiazza et al. |
| 10,457,970 B2 | 10/2019 | Caiazza |
| 2003/0166207 A1 | 9/2003 | Roessler et al. |
| 2004/0018590 A1 | 1/2004 | Gerngross et al. |
| 2004/0235127 A1 | 11/2004 | Metz |
| 2006/0253928 A1 | 11/2006 | Bakker et al. |
| 2006/0275904 A1 | 12/2006 | Ono et al. |
| 2009/0093033 A1 | 4/2009 | Luy |
| 2010/0016555 A1 | 1/2010 | Bobrowicz et al. |
| 2010/0034823 A1 | 2/2010 | Borhani et al. |
| 2010/0178298 A1 | 7/2010 | Lindhofer |
| 2010/0221763 A1 | 9/2010 | Matta et al. |
| 2010/0227363 A1 | 9/2010 | Bosh et al. |
| 2010/0233760 A1 | 9/2010 | Apt et al. |
| 2011/0118331 A1 | 5/2011 | Behr et al. |
| 2011/0195480 A1 | 8/2011 | Bayne et al. |
| 2011/0306075 A1 | 12/2011 | Bosques et al. |
| 2012/0322116 A1 | 12/2012 | Sakaguchi et al. |
| 2012/0328626 A1 | 12/2012 | Sethuraman et al. |
| 2013/0040897 A1 | 2/2013 | Aebi et al. |

(Continued)

FOREIGN PATENT DOCUMENTS

| | | |
|---|---|---|
| EP | 1414941 B1 | 10/2002 |
| EP | 2623588 A1 | 8/2013 |

(Continued)

OTHER PUBLICATIONS

Aebi, et al.: "Cloning and Characterization of the ALG3 Gene of Saccharomyces cerevisiae;"Glycobiology, 1996, vol. 6, No. 4, pp. 439-444.
Bayne, et al.: "Vaccination Against Influenza with Recombinant Hemagglutinin Expressed by Schizochytrium sp. Confers Protective Immunity"PLOS One, Apr. 2013, vol. 8, Issue 4, pp. E61790, 2-10.
Bobrowicz, et al.: "Engineering of an Artificial Glycosylation Pathway Blocked in Core Oligosaccharide Assembly in the Yeast Pichia pastoris: Production of Complex Humanized Glycoproteins with Terminal Galactose;"Glycobiology, 2004, vol. 14, No. 9, pp. 757-766.
Choi, et al.: "Use of Combinatorial Genetic Libraries to Humanize N-Linked Glycosylation in the Yeast Pichia pastoris;"PNAS, Apr. 29, 2003, vol. 100, No. 9, pp. 5022-5027.
Geijtenbeek, et al.: "Signalling Through C-Type Lectin Receptors: Shaping Immune Responses;" Nature Reviews | Immunology, Jul. 2009, vol. 9, pp. 465-479.

Primary Examiner — Maryam Monshipouri
(74) Attorney, Agent, or Firm — Wolf, Greenfield & Sacks, P.C.; Karen K. Chan

(57) ABSTRACT

The present invention provides recombinant cells that contain a genetic modification to at least one mannosyl transferase gene. As a result of the modification the cells produce a glycoprotein or glycopeptide that has an N-linked glycan profile that is simplified or more easily humanized. The glycoprotein or glycopeptide can have at least 25% fewer high mannose structures on than the glycoprotein or glycopeptide produced by a reference cell. In some embodiments the modification is a deletion or disruption of a mannosyl transferase gene, which can be in an alg3 gene. Therefore, the proteins produced are more useful for the production of therapeutic glycoproteins than those produced by species having foreign or plant-like patterns of glycosylation. The invention also provides compositions of the glycoproteins or glycopeptides and methods of making them.

28 Claims, 9 Drawing Sheets

Figure 1:
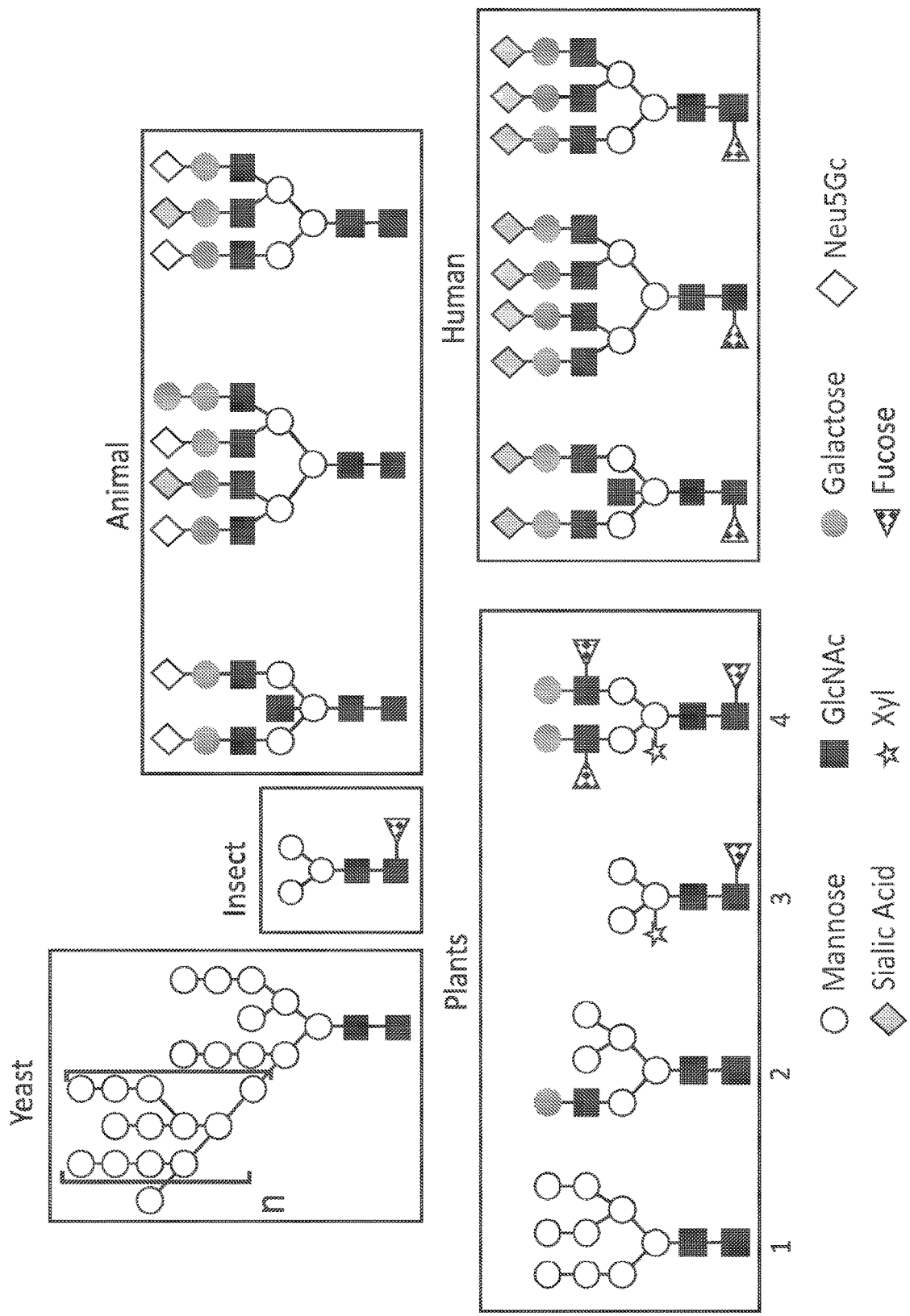

Specification includes a Sequence Listing.

(56) References Cited

U.S. PATENT DOCUMENTS

| | | |
|---|---|---|
| 2013/0231255 A1 | 9/2013 | Collins et al. |
| 2013/0323780 A1 | 12/2013 | Schneider et al. |
| 2015/0110826 A1 | 4/2015 | Bayne et al. |
| 2015/0132803 A1 | 5/2015 | Apt et al. |
| 2015/0376249 A1 | 12/2015 | Choi |
| 2016/0177255 A1 | 6/2016 | Radakovits et al. |
| 2016/0257965 A1 | 9/2016 | Caiazza et al. |
| 2017/0067058 A1 | 3/2017 | Yoneyama et al. |
| 2017/0247426 A1 | 8/2017 | Bulik et al. |
| 2017/0268015 A1 | 9/2017 | Caiazza et al. |
| 2018/0119193 A1 | 5/2018 | Caiazza |
| 2018/0201941 A1 | 7/2018 | Caiazza et al. |

FOREIGN PATENT DOCUMENTS

| | | |
|---|---|---|
| EP | 3265567 A0 | 1/2018 |
| WO | WO 2006/014685 A1 | 2/2006 |
| WO | WO 2007/006570 A2 | 1/2007 |
| WO | WO 2007/084922 A2 | 7/2007 |
| WO | WO 2013/144257 A1 | 10/2013 |
| WO | WO 2014/151318 A1 | 9/2014 |
| WO | WO 2015/179844 | 11/2015 |
| WO | WO 2012/120375 A2 | 9/2016 |
| WO | WO 2016/140925 A1 | 9/2016 |
| WO | WO 2017/161005 A1 | 9/2017 |
| WO | WO 2017/194699 A1 | 11/2017 |
| WO | WO 2018/085273 A1 | 5/2018 |
| WO | WO 2019/089077 A1 | 5/2019 |
| WO | WO 2019/173226 A1 | 9/2019 |
| WO | WO 2019/213069 A1 | 11/2019 |
| WO | WO 2019/213095 A1 | 11/2019 |

OTHER PUBLICATIONS

Hamilton and Gerngross: "*Glycosylation Engineering in Yeast: the Advent of Fully Humanized Yeast;*"Current Opinion in Biotechnology, 2007, vol. 18, pp. 387-392.

International Search Report dated Jul. 12, 2018 regarding PCT/US2018/030235.

International Search Report dated Jan. 19, 2018, regarding PCT/US2017/059304.

Nasab et al.: "*A combined system for engineering glycosylation efficiency and glycan structure in Saccharomyces cerevisiae*"; Appl Environ Microbiol, Nov. 30, 2012,vol. 79, No. 3, pp. 997-1007.

Orchard et al.: "*Rhodanine-3-acetic acid derivatives as inhibitors of fungal protein mannosyl transferase 1 (PMT1)*"; Bioorg Med Chem Lett, Aug. 2, 2004, vol. 14, No. 15, p. 3975-3978.

UNIPROT: "*P38179: Dol-P-Man:Man(5)GlcNAc(2)-PP-Dol alpha-1,3-mannosyltransferase*"; May 4, 2016, pp. 1-7. Retrieved from the Internet on Dec. 26, 2017: https://web.archive.org/web/20160504193836/http://www.uniprot.org/uniprot/P38179>.

Wildt and Gerngross: "*The Humanization of N-Glycosylation Pathways in Yeast;*" Nature Reviews | Microbiology, 2005, vol. 3, pp. 119-128.

Yokoyama et al.: "*Taxonomic rearrangement of the genus Schizochytrium sensu lato based on morphology, chemotaxonomic characteristics, and 18S rRNA gene phylogeny (Thraustochytriaceae, Labyrinthulomycetes): emendation for Schizochytrium and erection of Aurantiochytrium and Oblongichytrium gen. nov.*"; Mycoscience, Aug. 1, 2007, vol. 48, No. 4, pp. 199-211.

[No Author Listed], Approval of Humira II-adalimumab by EMEA, Jan. 1, 2004, XP055624077, Retrieved from the Internet: URL:https://www.ema.europa.eu/en/documents/scientific-discussion/humira-epar-scientific-discussion_en.pdf [retrieved on Sep. 19, 2019]. 25 pages.

[No Author Listed], Genbank 1N8Z_A, Chain A, Herceptin Fab (antibody)—Light Chain, ncbi.nlm.nih.gov/protein/28948772?sat=16&satkey=10451034. 2012. 2 pages.

[No Author Listed], Genbank AB557594.1, Expression vector beta-act-loxP-RFP-loxP-GFP DNA. 2010.

[No Author Listed], NCBI GenBank accession No. KC218923.1. Apr. 30, 2013.

[No Author Listed], NCBI GenBank accession No. DQ356659.1. Feb. 24, 2009.

[No Author Listed], NCBI GenBank accession No. JX978726.1. Jan. 9, 2015.

Altschul et al., Basic local alignment search tool. J Mol Biol. Oct. 5, 1990;215(3):403-10.

Becker et al., Isolation of the repertoire of VSG expression site containing telomeres of Trypanosoma brucei 427 using transformation-associated recombination in yeast. Genome Res. Nov. 2004;14(11):2319-29.

Chung et al., Insertional inactivation studies of the csmA and csmC genes of the green sulfur bacterium Chlorobium vibrioforme 8327: the chlorosome protein CsmA is required for viability but CsmC is dispensable. FEMS Microbiol Lett. Jul. 15, 1998;164(2):353-61.

Ferrante et al., An optimized, chemically regulated gene expression system for Chlamydomonas. PLoS One. Sep. 12, 2008;3(9):e3200. doi: 10.1371/journal.pone.0003200.

Garcia-Vedrenne et al., Development of genomic resources for a thraustochytrid pathogen and investigation of temperature influences on gene expression. PLoS One. Sep. 17, 2013;8(9):e74196. doi: 10.1371/journal.pone.0074196.

Gerrish et al., Pancreatic beta cell-specific transcription of the pdx-1 gene. The role of conserved upstream control regions and their hepatic nuclear factor 3beta sites. J Biol Chem. Feb. 4, 2000;275(5):3485-92.

Gibson et al., Enzymatic assembly of DNA molecules up to several hundred kilobases. Nat Methods. May 2009;6(5):343-5. doi: 10.1038/nmeth.1318. Epub Apr. 12, 2009.

Gibson, Enzymatic assembly of overlapping DNA fragments. Methods Enzymol. 2011;498:349-61. doi: 10.1016/B978-0-12-385120-8.00015-2.

Hellen et al., Internal ribosome entry sites in eukaryotic mRNA molecules. Genes Dev. Jul. 1, 2001;15(13):1593-612.

Henikoff et al., Amino acid substitution matrices from protein blocks. Proc Natl Acad Sci U S A. Nov. 15, 1992;89(22):10915-9.

Higo et al., Plant cis-acting regulatory DNA elements (PLACE) database: 1999. Nucleic Acids Res. Jan. 1, 1999;27(1):297-300.

Hirschmann et al., The multi-protein family of sulfotransferases in plants: composition, occurrence, substrate specificity, and functions. Front Plant Sci. Oct. 16, 2014;5:556. doi: 10.3389/fpls.2014.00556. eCollection 2014.

Isett et al., Twenty-four-well plate miniature bioreactor high-throughput system: assessment for microbial cultivations. Biotechnol Bioeng. Dec. 1, 2007;98(5):1017-28.

Ji et al., Genome Sequence of *Schizochytrium* sp. CCTCC M209059, an Effective Producer of Docosahexaenoic Acid-Rich Lipids. Genome Announc. Aug. 6, 2015;3(4). pii: e00819-15. doi: 10.1128/genomeA.00819-15.

Kai et al., Silencing of Carbohydrate Sulfotransferase 15 Hinders Murine Pulmonary Fibrosis Development. Mol Ther Nucleic Acids. Mar. 17, 2017;6:163-172. doi: 10.1016/j.omtn.2016.12.008. Epub Dec. 31, 2016.

Karlin et al., Applications and statistics for multiple high-scoring segments in molecular sequences. Proc Natl Acad Sci U S A. Jun. 15, 1993;90(12):5873-7.

Kellerman et al., Analysis of the primary structure and promoter function of a pyruvate decarboxylase gene (PDC1) from *Saccharomyces cerevisiae*. Nucleic Acids Res. Nov. 25, 1986;14(22):8963-77.

Kim et al., High cleavage efficiency of a 2A peptide derived from porcine teschovirus-1 in human cell lines, zebrafish and mice. PLoS One. 2011;6(4):e18556. doi: 10.1371/journal.pone.0018556. Epub Apr. 29, 2011.

Kindle et al., Stable nuclear transformation of Chlamydomonas using the Chlamydomonas gene for nitrate reductase. J Cell Biol. Dec. 1989;109(6 Pt 1):2589-601.

Kindle, High-frequency nuclear transformation of Chlamydomonas reinhardtii. Proc Natl Acad Sci U S A. Feb. 1990;87(3):1228-32.

Kobayashi et al., Increase of eicosapentaenoic acid in thraustochytrids through thraustochytrid ubiquitin promoter-driven expression of a

(56) References Cited

OTHER PUBLICATIONS fatty acid {delta}5 desaturase gene. Appl Environ Microbiol. Jun. 2011;77(11):3870-6. doi: 10.1128/AEM.02664-10. Epub Apr. 8, 2011.

Komar et al., Cellular IRES-mediated translation: the war of ITAFs in pathophysiological states. Cell Cycle. Jan. 15, 2011;10(2):229-40. Epub Jan. 15, 2011.

Lescot et al., PlantCARE, a database of plant cis-acting regulatory elements and a portal to tools for in silico analysis of promoter sequences. Nucleic Acids Res. Jan. 1, 2002;30(1):325-7.

Lippmeier et al., Characterization of both polyunsaturated fatty acid biosynthetic pathways in *Schizochytrium* sp. Lipids. Jul. 2009;44(7):621-30. doi: 10.1007/s11745-009-3311-9. Epub Jun. 3, 2009.

Lombard. The multiple evolutionary origins of the eukaryotic N-glycosylation pathway. Biology Direct. Aug. 4, 2016;11(36):1-31.

Matsuda et al., Analysis of Δ12-fatty acid desaturase function revealed that two distinct pathways are active for the synthesis of PUFAs in T. aureum ATCC 34304. J Lipid Res. Jun. 2012;53(6):1210-22. doi: 10.1194/jlr.M024935. Epub Feb. 26, 2012. Erratum in: J Lipid Res. Dec. 2012;53(12):2806.

McCarthy et al., Differential expression analysis of multifactor RNA-Seq experiments with respect to biological variation. Nucleic Acids Res. May 2012;40(10):4288-97. doi: 10.1093/nar/gks042. Epub Jan. 28, 2012.

Mendez-Alvarez et al., Transformation of Chlorobium limicola by a plasmid that confers the ability to utilize thiosulfate. J Bacteriol. Dec. 1994;176(23):7395-7. Erratum in: J Bacteriol Feb. 1995;177(4):1121.

Mogno et al., TATA is a modular component of synthetic promoters. Genome Res. Oct. 2010;20(10):1391-7. doi: 10.1101/gr.106732.110. Epub Jul. 13, 2010.

Mortazavi et al., Mapping and quantifying mammalian transcriptomes by RNA-Seq. Nat Methods. Jul. 2008;5(7):621-8. doi: 10.1038/nmeth.1226. Epub May 30, 2008.

Needleman et al., A general method applicable to the search for similarities in the amino acid sequence of two proteins. J Mol Biol. Mar. 1970;48(3):443-53.

Ohnuma et al., Polyethylene glycol (PEG)-mediated transient gene expression in a red alga, Cyanidioschyzon merolae 10D. Plant Cell Physiol. Jan. 2008;49(1):117-20. Epub Nov. 14, 2007.

Pasupathy et al., Direct plant gene delivery with a poly(amidoamine) dendrimer. Biotechnol J. Aug. 2008;3(8):1078-82. doi: 10.1002/biot.200800021.

Pearson et al., Improved tools for biological sequence comparison. Proc Natl Acad Sci U S A. Apr. 1988;85(8):2444-8.

Perrone et al., The Chlamydomonas IDA7 locus encodes a 140-kDa dynein intermediate chain required to assemble the I1 inner arm complex. Mol Biol Cell. Dec. 1998;9(12):3351-65.

Quinn et al., Copper response element and Crr1-dependent Ni(2+)-responsive promoter for induced, reversible gene expression in Chlamydomonas reinhardtii. Eukaryot Cell. Oct. 2003;2(5):995-1002.

Raghukumar, Thraustochytrid Marine Protists: production of PUFAs and Other Emerging Technologies. Mar Biotechnol (NY). Nov. 2008-Dec.;10(6):631-40. doi: 10.1007/s10126-008-9135-4. Epub Aug. 20, 2008.

Ranasinghe et al., An improved protocol for the isolation of total genomic DNA from Labyrinthulomycetes. Biotechnol Lett. Mar. 2015;37(3):685-90. doi: 10.1007/s10529-014-1712-1. Epub Oct. 30, 2014.

Rombauts et al., PlantCARE, a plant cis-acting regulatory element database. Nucleic Acids Res. Jan. 1, 1999;27(1):295-6.

Sakaguchi et al., Versatile transformation system that is applicable to both multiple transgene expression and gene targeting for Thraustochytrids. Appl Environ Microbiol. May 2012;78(9):3193-202. doi: 10.1128/AEM.07129-11. Epub Feb. 17, 2012.

Shagin et al., GFP-like proteins as ubiquitous metazoan superfamily: evolution of functional features and structural complexity. Mol Biol Evol. May 2004;21(5):841-50. Epub Feb. 12, 2004.

Shahmuradov et al., PlantProm: a database of plant promoter sequences. Nucleic Acids Res. Jan. 1, 2003;31(1):114-7.

Smith et al., Comparison of biosequences. Adv Appl Math. Dec. 1, 1981;2(4):482-9.

Trapnell et al., Differential gene and transcript expression analysis of RNA-seq experiments with TopHat and Cufflinks. Nat Protoc. Mar. 1, 2012;7(3):562-78. doi: 10.1038/nprot.2012.016. Erratum in: Nat Protoc. Oct. 2014;9(10):2513.

Watt et al., urg1: a uracil-regulatable promoter system for fission yeast with short induction and repression times. PLoS One. Jan. 16, 2008;3(1):e1428. doi: 10.1371/journal.pone.0001428.

Wolk et al., Construction of shuttle vectors capable of conjugative transfer from *Escherichia coli* to nitrogen-fixing filamentous cyanobacteria. Proc Natl Acad Sci U S A. Mar. 1984;81(5):1561-5.

Yamanishi et al., A genome-wide activity assessment of terminator regions in *Saccharomyces cerevisiae* provides a "terminatome" toolbox. ACS Synth Biol. Jun. 21, 2013;2(6):337-47. doi: 10.1021/sb300116y. Epub Feb. 20, 2013.

| Per-methylated mass (m/z)[1] | Text description of structures | Cartoon representation of structures[2] | % N-linked glycans[3] | |
|---|---|---|---|---|
| | | | PNGaseF | PNGaseA |
| 1171 | Man₅GlcNAc₂ | | 2.75 | n.d. |
| 1579 | Man₅GlcNAc₂ or | | 12.10 | 11.16 |
| 1668 | Sulph₁Man₅GlcNAc₂ or | | 5.14 | 7.01 |
| 1740 | Xyl₁Man₅GlcNAc₂ or | | 3.92 | 2.43 |
| 1783 | Man₆GlcNAc₂ | | 23.8 | 25.96 |
| 1872 | Sulph₁Man₆GlcNAc₂ | | 5.55 | 10.71 |
| 1987 | Man₇GlcNAc₂ | | 17.59 | 16.93 |
| 2033 | Sulph₁Xyl₁Man₆GlcNAc₂ or | | 2.14 | n.d. |
| 2076 | Sulph₁Man₇GlcNAc₂ | | 3.04 | 5.37 |
| 2191 | Man₈GlcNAc₂ or | | 10.12 | 8.26 |
| 2234 | Man₇GlcNAc₃ or | | 4.45 | 3.48 |
| 2395 | Man₉GlcNAc₂ | | 7.16 | 6.17 |
| 2438 | Man₈GlcNAc₃ or | | 2.27 | 1.82 |
| 2642 | Man₉GlcNAc₃ | | n.d. | 0.70 |

[1] All masses (mass+Na) are single-charged.
[2] Structures were assigned based on MS¹ mass, MS² fragmentation (CID) and general biosynthetic pathway of N-glycans
[3] Calculated from the area units of detected N-linked glycans; nd = not detected Legend – ■ - GlcNAc; ● - Man; □ - HexNAc; ✶ - Pentose; S - Sulfation

FIGURE 7

| Permethyl ated mass (m/z)[1] | Text description of structures | Cartoon representation of structures[2] | % N-linked glycans[3] | |
|---|---|---|---|---|
| | | | PNGaseF | PNGaseA |
| 1171 | Man3GlcNAc2 | | 40.62 | 40.56 |
| 1260 | Sulph1Man3GlcNAc2 | | 40.65 | 39.60 |
| 1375 | Man4GlcNAc2 | | 8.36 | 8.95 |
| 1579 | Man5GlcNAc2 | | 7.64 | 7.44 |
| 1783 | Man6GlcNAc2 | | 2.72 | 2.53 |

[1] All masses (mass+Na) are single-charged.
[2] Structures were assigned based on MS[1] mass, MS[1] fragmentation (CID) and general biosynthetic pathway of N-glycans
[3] Calculated from the area units of detected N-linked glycans; nd = not detected
Legend – ■ - GlcNAc; ● - Man; S - Sulfation

FIGURE 8

EXPRESSION OF MODIFIED GLYCOPROTEINS AND GLYCOPEPTIDES

CROSS-REFERENCE TO RELATED APPLICATIONS

This application is a continuation-in-part of U.S. application Ser. No. 15/799,785, filed Oct. 31, 2017, which claims the benefit of provisional application Ser. No. 62/416,086, filed Nov. 1, 2016, each of which is hereby incorporated by reference in its entirety, including all tables, figures, and claims.

INCORPORATION OF SEQUENCE LISTING

The material in the accompanying sequence listing is hereby incorporated by reference into this application. The accompanying sequence listing text file, name SG12060_2_Sequence_Listing.txt, was created on Apr. 27, 2018, and is 7 kb. The file can be assessed using Microsoft Word on a computer that uses Windows OS.

FIELD OF THE INVENTION

The invention involves the production of proteins and peptides having humanized or simplified N-glycan patterns, host cells, methods of producing the glycoproteins and glycopeptides, and expression cassettes and other tools useful in the methods.

BACKGROUND OF THE INVENTION

Microbial expression systems have numerous advantages for the production of useful proteins. While certain microbial systems are useful for producing simple proteins, such microbial systems would need to be improved for the efficient production of more complex proteins. The improvement of microbial cell specific productivities requires complex engineering, and substantial understanding and rewiring of the underlying microbial metabolism. An ideal strain would be genetically stable, have a high specific and volumetric productivity, form no by-products, and use a well-defined medium. These characteristics would allow for downstream processing with a limited number of steps.

Labyrinthulomycetes are robustly fermentable eukaryotic organisms. These heterotrophic microorganisms are recognized for their industrial ability to consume sugar and store large amounts of cellular oils as triglycerides; the most commercially important is docosahexaenoic acid (DHA), an omega-3 polyunsaturated fatty acid (PUFA) that is a major component of fish oil. These organisms produce oils that can be used in human and animal nutritional supplements, as well as for food fortification applications. These triglyceride oils can be produced in culture using inexpensive media.

Because of these desirable qualities it would be advantageous to have recombinant Labyrinthulomycetes cells that are able to produce a variety of proteins or therapeutic proteins, including therapeutic proteins and functional antibodies.

Many therapeutic proteins require N-linked glycosylation to function, optimally. The human pathway for synthesizing N-linked glycans differs from those of other mammals, invertebrates, plants, insects, and lower eukaryotes (such as yeast of fungi). This presents a problem when attempting to express human proteins in heterologous hosts, namely that the protein of interest will not contain human N-linked glycans, but instead be decorated with N-linked glycans that are endogenous to the heterologous host. This can result in a myriad of problems ranging from proteins that are allergenic, less active, inactive, less soluble, insoluble, unstable, unable to properly interact with biological targets. It would therefore be very useful to have a heterologous host system that is able to produce proteins containing human patterns of glycosylation or simplified glycosylation patterns that could be easily converted into human patterns.

SUMMARY OF THE INVENTION

The present invention provides recombinant host cells that contain a genetic modification in one or more genes that encode a mannosyl transferase. As a result of the modification the cells produce a glycoprotein or glycopeptide that has an N-linked glycan profile that is more humanized or human-like, or is simplified. In some embodiments the glycoprotein or glycopeptide has at least 25% fewer high mannose N-glycan structures on than the same glycoprotein or glycopeptide produced by a cell that does not have the modification. In some embodiments the genetic modification is a deletion, which can be in the alg3 gene, and the host cell can be a Labyrinthulomycete cell. Therefore, the heterologous glycoproteins and glycopeptides produced in the invention avoid many of the problems associated with the use of glycoproteins and glycopeptides having patterns of glycosylation of non-human species. The invention also provides compositions of the glycoproteins and glycopeptides, methods of making them, and nucleic acid constructs useful for the methods.

In a first aspect the invention provides a recombinant cell of the family Thraustochytriaceae having a nucleic acid molecule encoding a heterologous glycoprotein or glycopeptide, and a genetic modification to one or more gene(s) encoding a mannosyl transferase, wherein the cell produces a heterologous glycoprotein or glycopeptide having an N-linked glycan profile comprising at least 50% paucimannose N-glycan structures. In various embodiments the genetic modification can be a deletion, an insertion, a replacement, and a disruption, and the mannosyl transferase can be an alpha-1,3-mannosyl transferase, or a mannosyl transferase of the class EC 2.4.1.258. In some embodiments the heterologous glycoprotein or glycopeptide is an antibody, for example trastuzumab, eculizumab, natalizumab, cetuximab, omalizumab, usteinumab, panitumumab, and adalimumab, or a functional fragment of any of them. In one embodiment the heterologous glycoprotein or glycopeptide has an N-linked glycan profile having at least 50% fewer high mannose N-linked glycans than the N-linked glycan profile from a corresponding cell that does not comprise the mannosyl transferase deletion, or can have an N-linked glycan profile having less than 20% high mannose structures. In specific embodiments the cell can be from the family Thraustochytriaceae, and from one of the genera *Aurantiochytrium* sp., *Schizochytrium* sp., or *Thraustochytrium* sp. In some embodiments the glycoprotein or glycopeptide comprises at least 25% fewer xylose moieties than the cell that does not comprise the mannosyl transferase deletion. In some embodiments the glycoprotein or glycopeptide does not comprise N-linked glycans comprising xylose. The N-linked glycans can be at least 80% paucimannose structures, and/or can be at least 70% Man3. In another embodiment the N-linked glycan profile can have at least 70% fewer high mannose structures compared to a reference cell not comprising the genetic modification.

In another aspect the invention provides a method of producing a glycoprotein or glycopeptide that comprises a simplified N-glycan profile. The method involves performing a genetic modification to a gene that encodes a mannosyl transferase in a Thraustochytriaceae host cell; cultivating the host cell; and harvesting a glycoprotein or glycopeptide from the cell that has an N-linked glycan profile comprising at least 50% paucimannose structures. The genetic modification, the glycoprotein or glycopeptide, and the mannosyl tranferase enzyme can be any described herein. The glycoprotein or glycopeptide can have any N-linked glycan structure described herein, and the host cell can be a host cell of the invention as described herein.

In another aspect the invention provides a glycoprotein or glycopeptide composition having a simplified N-glycan profile, as described herein. The glycoprotein or glycopeptide can be any described herein, and can be derived from a recombinant cell of the family Thraustochytriaceae, or any host cell described herein.

In another aspect the invention provides a method of producing a glycoprotein or glycopeptide having an N-glycan profile comprising at least 75% man3 or man4 glycan structures. The method involves providing a recombinant cell of the family Thraustochytriaceae that produces a heterologous glycoprotein or glycopeptide and that further comprises a mannosyl transferase enzyme; contacting the recombinant cell with a molecule that reduces mannosyl transferase enzyme activity in the cell; thereby producing the glycoprotein or glycopeptide having an N-glycan profile comprising at least 75% man3 or man3/man4 glycan structures. In some embodiments the molecule that reduces the mannosyl transferase activity is an RNAi, which can be encoded by an exogenous nucleic acid comprised within the cell. The exogenous nucleic acid is comprised on a vector, or can be integrated into the genome of the cell. The recombinant cell can be comprised within a medium that comprises the RNAi, and the molecule that reduces the mannosyl transferase activity is an inhibitor of mannosyl transferase. The inhibitor can be produced by one or more nucleic acid molecules comprised in the cell. In one embodiment the inhibitor is rhodanine-3-acetic acid, or 5-[[3-(1-phenylethoxy)-4-(2-phenylethoxy)phenyl]methylene]-4-oxo-2-thioxo-3-thiazolidineacetic acid (5a). The recombinant cell of the invention can be comprised within a medium that comprises the inhibitor.

DETAILED DESCRIPTION OF THE DRAWINGS

FIG. 1 provides a diagram illustrating the types of glycans produced in various types of organisms. The diagram illustrates that yeast has a hypermannose structure. Also illustrated are animal glycans, two of which have a Man3 core structure in a complex glycan. The plant glycans illustrated have either a high mannose structure or a Man3 core structure. Two human glycans are also illustrated having a Man3 core structure in a complex glycan structure. Some glycan structures are hybrid complex, such as that illustrated as the second plant glycan, which has complex structure extending from Man2 and a high mannose structure extending from Man3.

Figure 2:
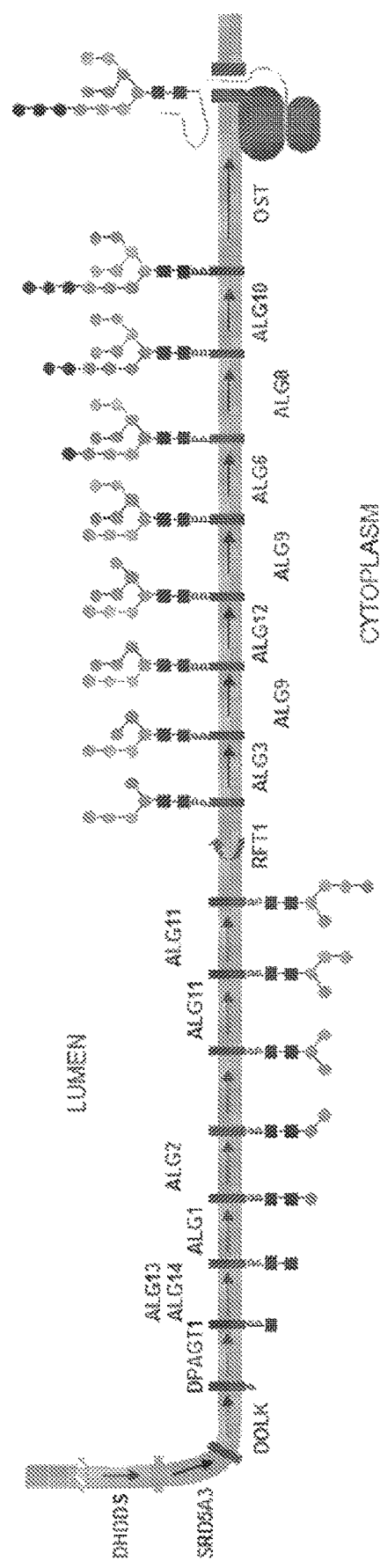

FIG. 2 provides a schematic illustration of ER N-linked glycosylation from *Saccharomyces cerevisiae*.

Figure 3A:
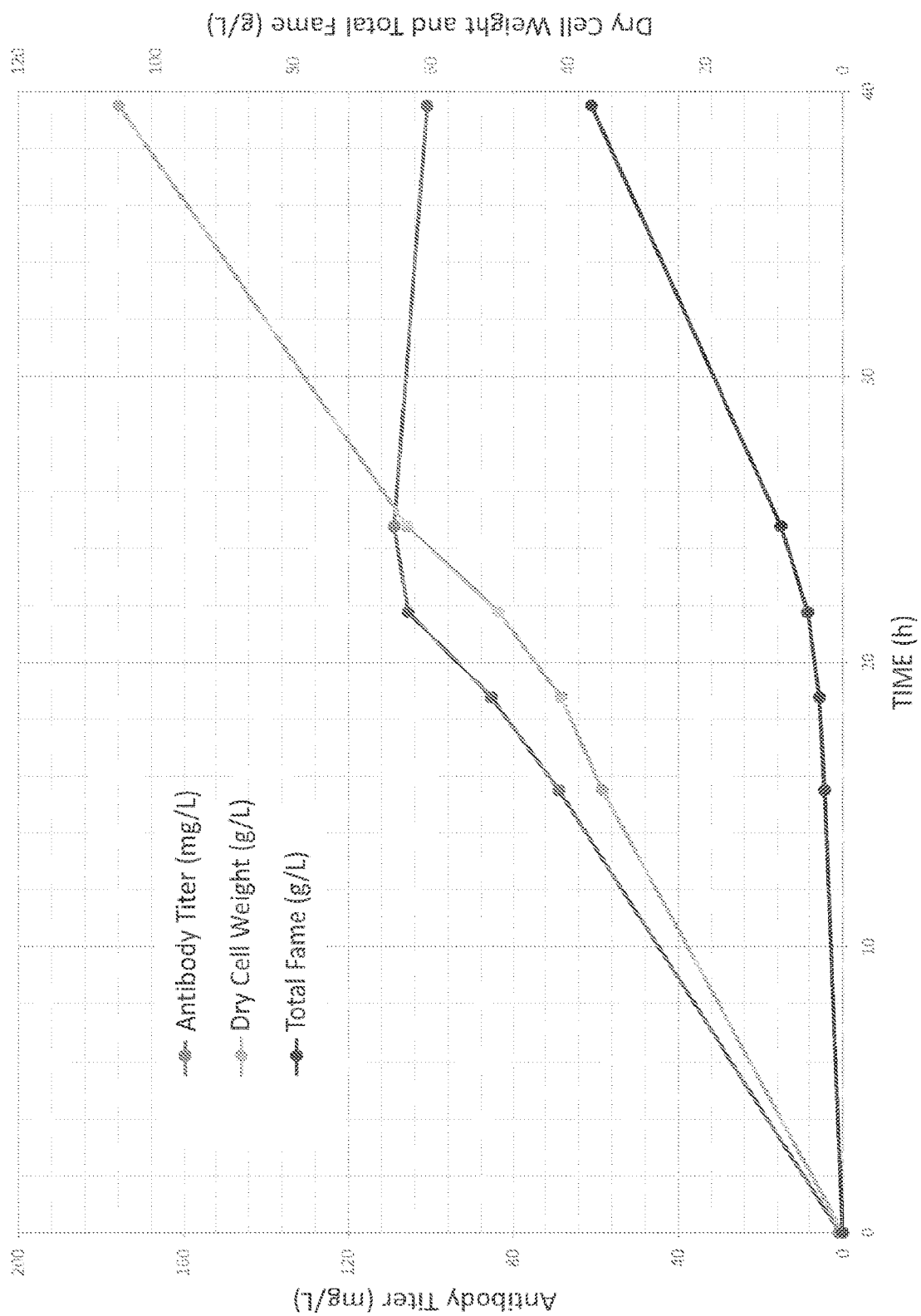
Figure 3D:
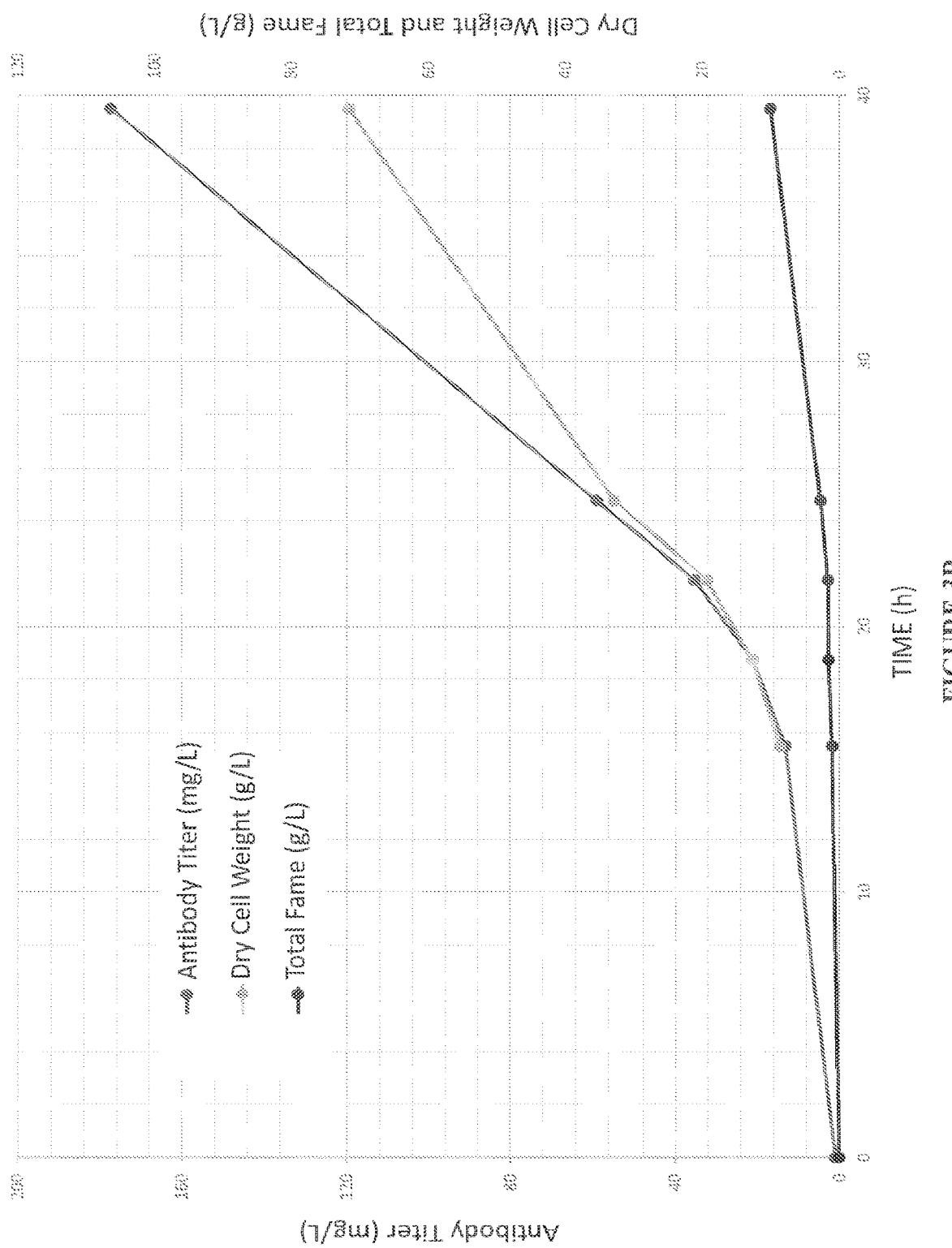

FIGS. 3A-3B, FIG. 3A provides a graphical illustration of the production of antibody (mg/L), biomass as dry cell weight (g/L) and total FAME (g/L) as part of biomass obtained in a fermentation with the background strain containing Alg3 (Alg3+). FIG. 3B provides the comparative graphical illustration of the fermentation with the modified, Alg3 deletion (Alg3−).

Figure 4:
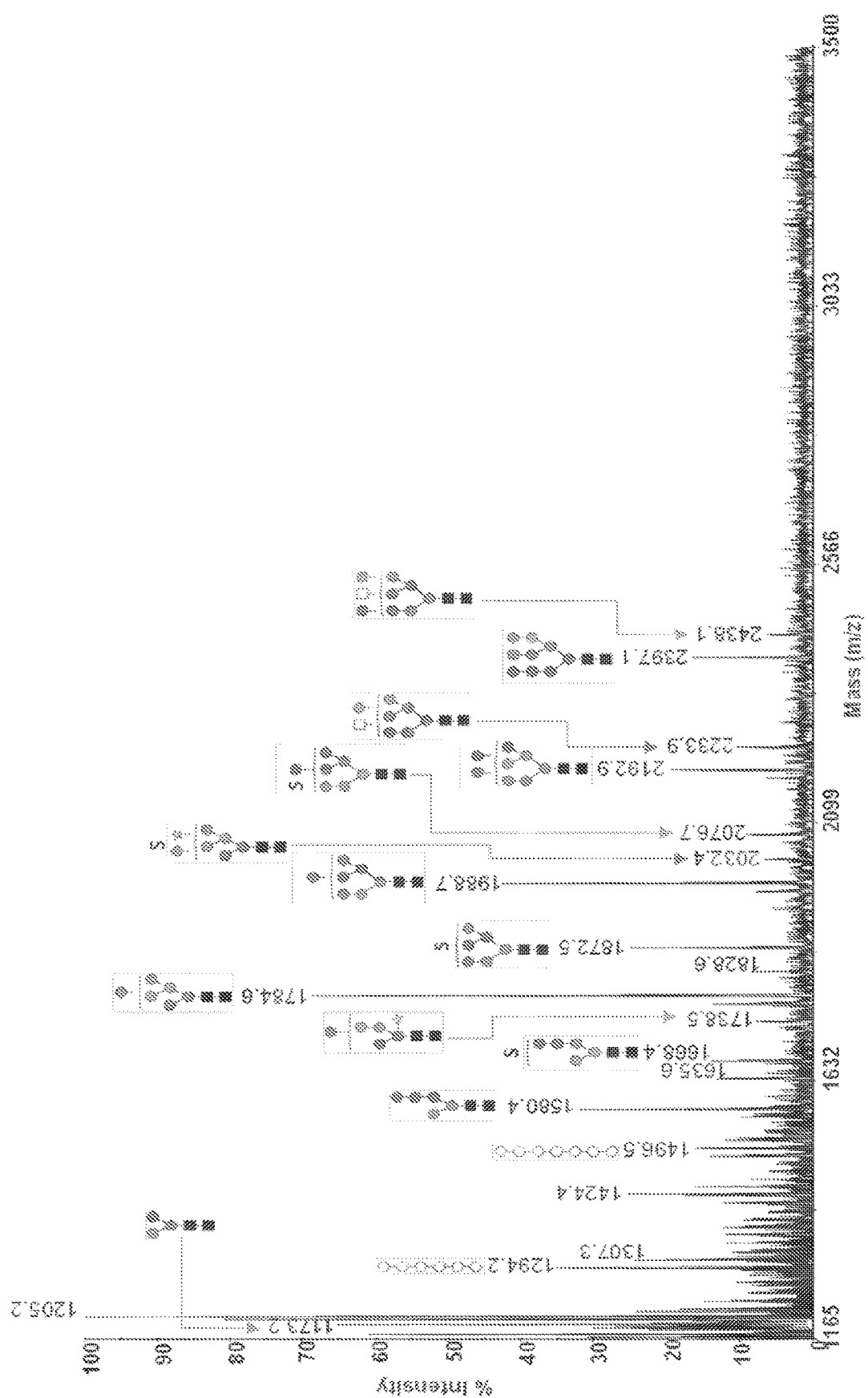

FIG. 4 illustrates the N-linked glycan profile on a specific glycoprotein antibody (trastuzumab) produced by the Alg3+ strain. MALDI-MS results of permethylated glycans released from trastuzumab antibody by PNGaseF produced by the Alg3+ organism. Modification occurred at the N-linked glycopeptide $^{323}$EEQY$\underline{\text{N}}$STYR$^{331}$. Legend: ■—GlcNAc (dark square); ●—Man (dark circle); ○—Hex (open circle); □—HexNAc (open square); ☆—Xylose (star); S—Sulfation.

Figure 5:
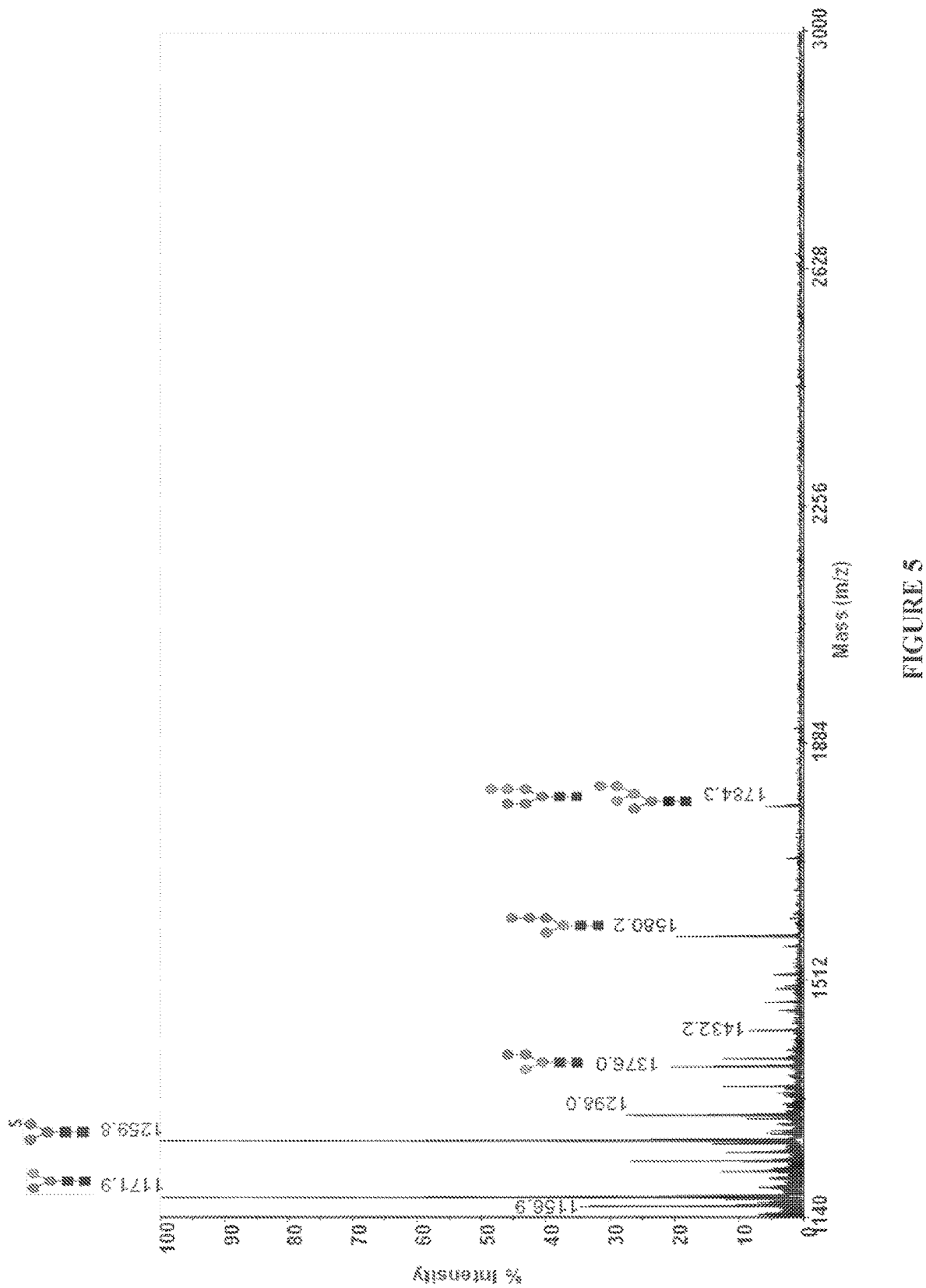

FIG. 5 illustrates the comparative N-linked glycan profile of the same glycoprotein as FIG. 4 but with the Alg3− deletion strain. The resultant profile shows a high preponderance of Man3 glycan structures. Modification occurred at the N-linked glycopeptide $^{32}$EEQYNSTYR$^{331}$. Legend: ■—GlcNAc (dark square); ●—Man (dark circle); ○—Hex (open circle); □—HexNAc (open square); ☆—Xylose (star); S—Sulfation.

Figure 6A:
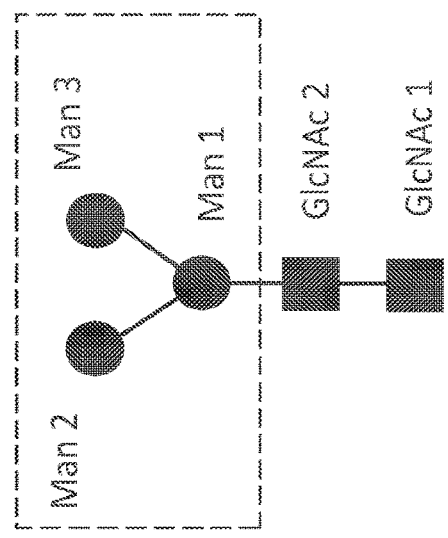
Figure 6B:

FIGS. 6A-6B, FIG. 6A provides a schematic illustration of the structure of man3 core glycan structure. FIG. 6B provides a similar illustration of man4 core glycan structure.

FIG. 7 shows N-linked glycans from the alg3+ strain detected by MALDI TOF/TOF MS. Structures were assigned based on ESI-MS$^n$ fragmentation of individual peaks. Numerous high mannose (Man5 and higher) core structures are seen.

FIG. 8 shows N-linked glycans from the alg3− strain detected by MALDI TOF/TOF MS and structures were assigned based on ESI-MS$^n$ fragmentation of individual peaks.

DETAILED DESCRIPTION OF THE INVENTION

The present invention provides recombinant host cells or organisms that contain a genetic modification that enables the cells or organisms to produce proteins or peptides having more Man3 or Man4 glycan core structures, and therefore more acceptable to human patients or easily convertible into human-like glycosylation patterns. The modification can be the functional deletion or disruption of a mannosyl transferase activity, e.g. via the deletion or disruption of a gene that encodes a mannosyl transferase enzyme. The cells or organisms produce glycomolecules that have an N-glycan profile that is simplified and convertible into a human-like glycosylation pattern. The glycomolecules can therefore avoid the problems that have been associated with the use of therapeutic proteins produced by heterologous hosts and can produce the simplified pattern more easily. The glycomolecules of the invention can therefore be less allergenic, have improved immunological properties, have higher biological activity and stability, be more soluble, and interact more effectively with biological targets. The glycomolecule in any embodiment herein can be a glycoprotein, glycopeptide, or glycolipid. A glycan profile as used herein can refer to an N-linked glycan profile, an O-linked glycan profile, or both. The glycan profile can include all glycans associated with a heterologous protein produced in a cell, including simplified (Man3 and/or Man4) glycans, as well as hybrid-type and complex-type glycan structures.

The host cells or organisms of the invention provide the advantage of producing the desired glycomolecule while requiring a minimum of genetic modifications. It was discovered unexpectedly that by using host cells of the family Thraustochytriaceae, it is only necessary to perform the genetic modification to the alg3 gene to obtain the beneficial effects. The host cell or organism can therefore produce a heterologous glycoprotein or glycopeptide that produces an N-glycan profile having a high amount of paucimannose structures. In any of the embodiments the host cells of the invention can therefore have a single deletion (or other genetic modification described herein) of a mannosyl transferase gene, which can result in a host cell or organism able to produce a heterologous glycoprotein or glycopeptide having an N-linked glycan profile described herein.

In any of the embodiments the host cells of the invention can produce a glycoprotein or glycopeptide having an N-linked glycan profile having a high level of Man3 and/or Man4 core structure. Thus, the N-linked glycan profile can have at least 10% or at least 20% or at least 30%, or at least 40%, or at least 45%, or at least 50%, or at least 55%, or at least 60%, or at least 65%, or at least 70%, or at least 75%, or at least 80%, or at least 85%, or at least 90% or 50-90%, or 60-70%, or 70-80%, or 60-90% or 65-90% or 75-85% or 75-90% or 75-95% Man3 structures in one embodiment, Man4 structures in another embodiment, or a combination of Man3 and Man4 (or simplified) glycan structures in another embodiment. In other embodiments the heterologous glycoprotein or glycopeptide has an N-glycan profile containing at least 20% more, or at least 30% more, or at least 40% more, or at least 50% more, or at least 60% more, or at least 70% more or at least 80% more, or at least 90% more, or at least 2× more, or at least 3× more Man3 structures in one embodiment, Man4 structures in another embodiment, or a combination of Man3 and Man4 structures in another embodiment, compared to a reference cell not having the genetic modification to a mannosyl transferase gene and cultivated under the same conditions. Therefore, the invention allows the glycoprotein or glycopeptide to be produced with higher amounts of Man3 and/or Man4 core structures more efficiently and with less effort by selecting a host with greater abilities to produce these structures. In any of the embodiments, the GlcNAc2Man3 and/or GlcNAc2Man4 core structures (or simply Man3 and/or Man4 referring to same) can be produced without any fucose, xylose, or other carbohydrate moieties attached to the core structure.

Man3GlcNAc2 and/or Man4GlcNAc2 core glycan structures are designated paucimannose and are illustrated in FIGS. 6a and 6b. Thus, paucimannose structures can have the structure Man3GlcNAc2 and/or Man4GlcNAc2, and may or may not have xylose, fucose, galactose, or other hexose moieties attached to the core, or sulfate modification(s), or any combination or sub-combination of them. Other glycans can contain these core structures and also have additional oligosaccharide residues on the core (e.g. GlcNAc, xylose, galactose, sialic acid, or fucose), and some exemplary structures are illustrated in FIG. 1. In other embodiments the cells can produce a heterologous glycoprotein or glycopeptide having reduced high mannose structures as described herein and also increased Man3 and/or Man4 core structures as described herein—i.e. the reduction in high mannose structures can be accompanied by the increase in Man3 and/or Man4 core structures.

Another advantage of the invention is that unlike (for example) plant cells, the cells of the family Thraustochytriaceae are robust enough to be easily scalable to large volumes as well as for use in fermenters.

In any of the embodiments the host cells or organisms of the invention can contain a minimum of genetic modifications. In any of the embodiments the host cells or organisms of the invention do not comprise a disruption or deletion of a gene encoding an alpha-1,6-mannosyltransferase, or the cells can contain only wild-type alpha-1,6-mannosyltransferases, which are not overexpressed or genetically modified. In various embodiments the cells do not need, or lack, a genetic modification of protein mannosyltransferase genes (PMTs) (e.g. deletions or disruptions); do not require the presence or use of Pmtp inhibitors to produce the amounts of Man3 and/or Man4 core structures described herein in the heterologous glycomolecule. The cells can produce the heterologous glycoproteins or glycopeptides described herein without the presence or use of any mannosidase (e.g. alpha-1,2-mannosidase to reduce high mannose core structures), and do not require or have a genetic modification to any beta-mannosyltransferase gene (e.g. deletion or disruption of BMT1, BMT2, BMT3, or BMT4). The cells of the invention also can lack any exogenous genes for carbohydrate transfer or biosynthesis (e.g. a galactosyltransferase) or an exogenous gamma-zein protein (which can direct a heterologous protein to the endoplasmic reticulum-derived protein bodies).

In any of the embodiments the host cells or organisms of the invention can contain a genetic modification only to a single gene encoding a mannosyl transferase enzyme. In any of the embodiments the single gene can be the alg3 gene (which can have multiple copies, and each can have a modification). In any of the embodiments all genes encoding a mannosyl transferase (except alg3 gene(s)) can be wild-type genes and can be present on and/or expressed from the genome, e.g. the host cell or organism can express the wild type alg11 gene, and can also have no expression of a mannosyl transferase from a plasmid or other nucleic acid construct. The host cell also expresses the heterologous glycoprotein or glycopeptide with the amounts of Man3 and/or Man4 core structures as described herein.

In any of the embodiments the cells can also comprise or express no heterologous enzymes. For example, the host cells or organisms of the invention do not require and can contain no heterologous flippases, and/or no heterologous mannosidases, and/or no overexpressed homologous or wild-type mannosidases are needed to produce the heterologous glycomolecule having the glycan profiles described herein. In other embodiments the cells can also contain no heterologous glycolipid translocation protein, examples including but not limited to Rft1 and/or Rft1p. Also, any of the embodiments of the host cells or organisms of the invention can contain no overexpression of wild-type or exogenous flippases or wild-type or exogenous glycolipid translocation protein(s), or any of the enzymes described above. The host cells also do not have or require the deletion or disruption of the ATT1 (acquired thermotolerance 1) gene; and does not have or require the deletion or disruption of the OCH1 (Outer Chain) gene; and does not have or require the deletion or disruption of an osteosarcoma gene (e.g. OS-9). The host cells can have natural, wild-type genes for all of these genes. The host cells can also not comprise or express any recombinant, heterologous, or exogenous GnTI or GnTII genes, proteins, or catalytic subunits. The host cells can also not have any mutations to reduce or eliminate endogenous protease activity.

The Labyrinthulomycetes are single-celled marine decomposers that generally consume non-living plant, algal, and animal matter. They are ubiquitous and abundant, particularly on dead vegetation and in salt marshes and mangrove swamps. In some embodiments the recombinant host cells or organisms of the invention are microorganisms of the class Labyrinthulomycetes, and can be from the taxonomic family Thraustochytriaceae, which family includes but is not limited to any one or more of the genera *Thraustochytrium, Japonochytrium, Aurantiochytrium, Aplanochytrium, Sycyoidochytrium, Botryochytrium, Parietichytrium, Oblongochytrium, Schizochytrium, Ulkenia,* and *Elina,* or any combination or sub-combination of them, which is disclosed as if set forth fully herein in all possible combinations.

While the classification of the Thraustochytrids and Labyrinthulids has evolved over the years, for the purposes of the present application. "Labyrinthulomycetes" is a comprehensive term that includes microorganisms of the Orders Thraustochytriales and Labyrinthulid. Organisms of the Order Thraustochytriales or Order Labyrinthulid are useful in the invention and include (without limitation) the genera *Althornia, Aplanochytrium, Aurantiochytrium, Botyrochytrium, Corallochytrium, Diplophryids, Diplophrys, Elina, Japonochytrium, Labyrinthula, Labryinthuloides, Oblongichytrium, Pyrrhosorus, Schizochytrium, Thraustochytrium*, and *Ulkenia*. In some examples the microorganism is from a genus including, but not limited to, *Thraustochytrium, Labyrinthuloides, Japonochytrium*, and *Schizochytrium*. Alternatively, a host Labyrinthulomycetes microorganism can be from a genus including, but not limited to, *Aurantiochytrium, Oblongichytrium*, and *Ulkenia*.

Examples of suitable microbial species within the genera include, but are not limited to: any *Schizochytrium* species, including, but not limited to, *Schizochytrium aggregatum, Schizochytrium limacinum, Schizochytrium minutum, Schizochytrium mangrovei, Schizochytrium marinum, Schizochytrium octosporum*, and any *Aurantiochytrium* species, any *Thraustochytrium* species (including former *Ulkenia* species such as *U. visurgensis, U. amoeboida, U. sarkariana, U. profunda, U. radiata, U. minuta* and *Ulkenia* sp. BP-5601), and including *Thraustochytrium striatum, Thraustochytrium aureum, Thraustochytrium roseum*; and any *Japonochytrium* species. Strains of the family Thraustochytriaceae that may be particularly suitable for the presently disclosed invention include, but are not limited to: *Schizochytrium* sp. (S31) (ATCC 20888); *Schizochytrium* sp. (S8) (ATCC 20889); *Schizochytrium* sp. (LC-RM) (ATCC 18915); *Schizochytrium* sp. (SR21); *Schizochytrium aggregatum* (ATCC 28209); *Schizochytrium limacinum* (IFO 32693); *Thraustochytrium* sp. 23B ATCC 20891; *Thraustochytrium striatum* ATCC 24473; *Thraustochytrium aureum* ATCC 34304); *Thraustochytrium roseum*(ATCC 28210; and *Japonochytrium* sp. LI ATCC 28207. In some embodiments the recombinant host cell of the invention can be selected from an *Aurantiochytrium* or a *Schizochytrium* or a *Thraustochytrium*, or all of the three groups together. The recombinant host cells of the invention can also be a yeast cell, such as a yeast selected from the genus *Saccharomyces* or *Candida* or *Pichia*. The recombinant host cell of the invention can be selected from any combination of the above groups, which are hereby disclosed as every possible combination as if set forth fully herein. The recombinant host cell of the invention can be selected from any combination of the above taxonomic groups, which are hereby disclosed as every possible combination or sub-combination as if set forth fully herein.

Labyrinthulomycetes produce proteins having a variety of N-linked glycan structures that contain high mannose structures and may also contain xylose or other hexose modifications. The N-glycan profile of glycoproteins produced by the Labyrinthulomycetes is more similar to that plants than humans and some types of glycans produced in different organisms are shown in FIG. 1. Therefore, native glycosylation patterns produced by these organisms are not optimal for a human patient because the glycosylation patterns are associated with the above-mentioned problems.

The modification(s) comprised in the recombinant cells of the invention can include one or more manipulation(s) of a host cell's genome or proteome using the techniques of molecular biology or biotechnology. The modification can change the genetic makeup of the cells, including the transformation of heterologous genes to produce improved or novel organisms. The modification can be a genetic modification, for example, the addition, deletion, disruption, modification, inactivation, or optimization of one or more genes. When a gene is added it can be a heterologous gene. e.g. a gene and regulatory sequences encoding a heterologous protein or peptide or antibody or immunoglobulin, which can be a functional and/or assembled and can, optionally, be overexpressed in the cell. The protein or peptide produced by the cell can be glycosylated, as described herein. The protein or peptide can be a therapeutic protein or peptide (e.g. an antibody), meaning that it is useful in the treatment or alleviation of any human or animal disease or medical condition.

In some embodiments the modification can be the functional modification of an enzyme. In various embodiments the functional modification can be the modification of one or more enzyme(s) in the glycosylation pathway. A functional modification is a modification that results in the change in the activity of an enzyme. A functional modification can be one or more mutations in the sequence of a gene, which results in an increase or reduction of the activity of the enzyme (e.g. a mannosyl transferase). In some embodiments the enzyme activity can be reduced by at least 10% or at least 15% or at least 20% or at least 25% compared to unmodified enzyme. In other embodiments the functional modification can be the inclusion of a gene that encodes an inhibitor or a suicide substrate directed to the enzyme which is expressed in the organism and binds the enzyme, and thereby inhibits, reduces, or eliminates its activity (by suicide inhibition, as one example).

The cells of the invention can therefore be recombinant cells, which are cells that contain a recombinant nucleic acid. The recombinant nucleic acid can encode a functional protein that is expressed in, and optionally secreted from, the recombinant cell. The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule can include any of: 1) a nucleic acid molecule that has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) include conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

When applied to organisms, the terms "transgenic" "transformed" or "recombinant" or "engineered" or "genetically engineered" refer to organisms that have been manipulated by introduction of an exogenous or recombinant nucleic acid sequence into the organism, or by the manipulation of native sequences, which are therefore then recombinant (e.g. by mutation of sequences, deletions, insertions, replacements, and other manipulations described below). In some embodiments the exogenous or recombinant nucleic acid can express a heterologous protein product. Non-limiting examples of such manipulations include gene knockouts, targeted mutations and gene replacement, gene replacement, promoter replacement, deletions or insertions, disruptions in a gene or regulatory sequence, as well as introduction of transgenes into the organism. For example, a transgenic microorganism can include an introduced exogenous regulatory sequence operably linked to an endogenous gene of the transgenic microorganism. Recombinant or genetically engineered organisms can also be organisms into which constructs for gene "knock down," deletion, or disruption have been introduced. Such constructs include, but are not limited to, RNAi, microRNA, shRNA, antisense, and ribozyme constructs. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome, or on a vector or other nucleic acid construct. As used herein, "recombinant microorganism" or "recombinant host cell" includes progeny or derivatives of the recombinant microorganisms of the disclosure. Because certain modifications may occur in succeeding generations from either mutation or environmental influences, such progeny or derivatives may not, in fact, be identical to the parent cell, but are still included within the scope of the term as used herein.

Glycoproteins and N-Glycan Profile

Many proteins produced by living organisms are modified by glycosylation, which occurs in specific patterns depending on the species of organism. These glycosylation patterns are important for their function as cellular recognition signals and to prevent an immune response against the protein, for protein folding, and for stability. N-linked glycan (or N-glycan) profiles refers to the specific glycosylation patterns present on a particular glycoprotein or glycopeptide (or group of glycoproteins or glycopeptides). The N-glycan profile of a glycoprotein or glycopeptide describes the number and structure of oligosaccharides that are associated with the particular glycoprotein or glycopeptide. FIGS. 4 and 5 show examples of N-glycan profiles for an antibody made in Alg+ and Alg3− cells, as well as FIGS. 7 and 8. In some embodiments the glycoprotein produced by the cells of the invention is a glycosylated therapeutic protein, such as a peptide or antibody. Monoclonal antibodies and immunoglobulins are just two of many categories of proteins that the invention can be applied to.

N-linked glycans (or N-glycans) are complex and diverse oligosaccharide chains attached to an asparagine residue of a polypeptide chain. In some embodiments the consensus peptide sequence Asn-X-Thr/Ser is glycosylated, where X is optionally present and can be any amino acid except proline and Thr/Ser is either threonine or serine. Yeast and mammalian biosynthetic pathways of N-linked glycans have been elucidated. The initial steps involve the synthesis of a lipid-linked oligosaccharide precursor structure that is transferred en bloc to nascent proteins in the ER. Typically, transfer of $Glc_3Man_9GlcNAc_2$ to Asn is followed by glucose trimming in the ER. Subsequent cycles of glucose re-addition and removal participate in quality control of protein-folding. The processed high-mannose $GlcNAc_2Man_5$ N-glycan serves as a substrate for the diversification of N-glycans in the Golgi.

Methods of determining the N-glycan profile of a glycoprotein or glycopeptide are known in the art and include, but are not limited to, fluorescently labeling N-glycans that are produced in a method and analyzed using liquid chromatography coupled to fluorescent detection. Methods of determining the N-glycan profile can involve steps of denaturation (e.g. by digestion with trypsin and reduction of disulfide bonds with DTT or mercaptoethanol), deglycosylation (e.g., by treatment with an endoglycosidase (e.g. PNGase) or use of hydrazinolysis or beta-elimination), optional purification (e.g. using a reverse phase C8 and C18 column), optional fluorescent labeling (e.g. using a Schiff base or carbamate), and optional solid phase extraction (e.g. with hydrophilic resins functionalized with amide, diol or microcrystalline cellulose), or analysis using MALDI TOF/TOF and ESI-MS, or MALDI quadrupole ion trap-TOFMS/MS. But persons of ordinary skill understand other methods of determining the N-glycan profile of a glycoprotein or glycopeptide, and the method provided in the examples infra. (e.g. Ex. 9) is one such method that can be applied in the invention, which involves denaturation, deglycosylation (e.g. with PNGaseF and PNGaseA), and analysis using MALDI TOF/TOF and ESI-MS. Examples of N-glycan profiles analysis are shown in FIG. 4 and FIG. 5. In another embodiment determination of the N-glycan profile can be done by performing deglycosylation with PNGaseF and PNGaseA, followed by MALDI TOF/TOF MS. In a further method, denaturation can be added prior to the deglycosylation step.

By a "high mannose structure" is meant a structure having 5 or more, or 5-6 or 5-9 or 5-11 or 5-20 or 5-35 or 5-50 or 10-20 or 10-30 or 10-50 mannose residues, which can also have a $GlcNAc_2$ stem (e.g., see FIG. 1 and FIG. 6). Such embodiments can be represented as, for example. $Man_5GlcNAc_2$ or $Man_9GlcNAc_2$, or any other symbol indicating 5 or 9 or 5-9 or 5-10 or 5-11 or 5-15 or 5-20 or 5-25 or 5-50 or any number of mannose residues as indicated linked to two GlcNAc, and examples are shown in FIGS. 1 and 4-5. FIG. 1 illustrates some examples of high mannose structures and N-glycan structures in yeast and plant categories. By a molecule having a stated percentage of high mannose structures is meant that, of the total N-glycan structures on the molecule, the stated percentage of the structures are high mannose structure. Thus, when a glycoprotein has less than 50% high mannose structures it is meant that, of the total number of N-glycan structures on the glycoprotein molecules, less than 50% of them contain a high mannose structure. Any of the high mannose structures can be sulfated or unsulfated. N-glycan structures, including high mannose structures, can also contain xylose residues, or other hexose modifications, meaning that one or more of the residues in the structure has a xylose or other hexose residue appended to it, for example as depicted in structures #3 and #4 in the plant N-glycans of FIG. 1. The xylose/hexose modification can be on any of Man1, Man2, or Man3, per FIG. 6 and/or can also be on $GlcNAc_1$ or $GlcNAc_2$.

In some embodiments the cells of the invention having the genetic modification to a mannosyl transferase gene produce a glycoprotein or glycopeptide having an N-linked glycan profile having at least 10% fewer, or at least 15% fewer, or at least 20% fewer, or at least 25% fewer, or at least 30% fewer, or at least 35% fewer, or at least 40% fewer, or at least 45% fewer, or at least 50% fewer, or at least 60% fewer, or at least 70% fewer, or at least 80% fewer or at least 90% fewer high mannose structures and/or fewer complex glycans compared to the same glycoprotein or glycopeptide produced by a corresponding cell (a reference cell) not having the genetic modification and cultured under the same conditions (which can be deletion or disruption of a mannosyl transferase gene). In various embodiments the observed effect of the genetic modification can be a reduction or other change in high mannose structures, or can be an increase in Man3 and/or Man4 core structures, or both, on the glycoprotein or glycopeptide of interest.

Glycoproteins and glycopeptides that are useful in biologics for use in humans can be those that have N-glycan profiles that are simplified or more easily humanized. Glycoproteins and glycopeptides that have a simplified N-glycan structures are also useful as they can be an effective starting point for the synthesis of more complex humanized N-glycan structures. Simplified N-glycan structures are man3 or man4 structures attached to the GlcNAc$_2$ stem, i.e. a Man3 or Man4 core structure as illustrated in FIG. 6a-b. These simplified structures can also, optionally, contain a fucose residue attached to any of the mannose or GlcNAc residues. These structures can also be sulfated or unsulfated on any residue. These structures can also lack xylose on any residue or all residues, and can also lack any other hexose modification on any residue or all residues. The recombinant cells or organisms of the invention can produce glycoproteins or glycopeptides having a simplified N-glycan structures, and in higher amounts.

Human glycosylation patterns commonly include man3 and/or man4 glycan structures attached to the GlcNAc$_2$ stem (the Man3 or Man4 core), and can also be complex glycan structures, i.e. have any one or more of 1) three or four additional GlcNAc residues present on man2 or man3; 2) 2, 3, or 4 galactose residues present on the GlcNAc residues; 3) 2, 3, or 4 sialic acid residues present on the galactose residues; and optionally N-acetyleuramic acid (Neu5Gc) residues present on the galactose residues. These embodiments are illustrated in FIG. 1. Complex glycan structures feature GlcNAc, galactose, sialic acid, or Neu5Gc extending from Man2 or Man3 of the core structure.

In various embodiments more than 20% or more than 25% or more than 30%, or more than 40%, or more than 50%, or more than 60%, or more than 70%, or more than 80%, or more than 85%, or more than 90% or 50-70% or 50-90% or 60-70% or 70-80% or 60-90% of the N-glycan structures on the glycoproteins or glycopeptides produced by the cells of the invention are simplified N-glycan structures. Any of the glycoproteins or glycopeptides produced according to the invention can also lack xylose or another hexose on Man1, Man2, Man3, Man4 (if present), GlcNAc1, or GlcNAc$_2$ (FIG. 6), or contain no residues modified with xylose or another hexose. The simplified glycoprotein or glycopeptide may or may not contain a fucose residue, which if present can be appended to the first or second GlcNAc on the stem. High mannose structures and simplified (e.g. Man3 and/or Man4) structures can be sulfated or unsulfated. The glycoproteins or glycopeptides produced can be useful themselves, or be useful as precursors to further glycol-engineering to further modify the N-glycan profile, for example to further humanize it or make it closer to a human pattern.

Nucleic Acid Constructs

Nucleic acids encoding the heterologous glycoproteins or glycopeptides produced by the cells of the invention can be integrated into the genome of the organism. They can also be expressed from an expression cassette or other nucleic acid construct present in the cell as are known in the art, and which can be transformed into the cell. Examples include, but are not limited to, a plasmid, cosmid, virus, autonomously replicating polynucleotide molecule, phage, linear or circular single-stranded or double-stranded nucleic acid molecule, artificial chromosome, or other nucleic acid construct, DNA or RNA polynucleotide molecule, derived from any source, capable of genomic integration or autonomous replication, comprising a nucleic acid molecule where one or more nucleic acid sequences has been linked in a functionally operative manner, i.e. operably linked. Constructs used in the cells of the invention can also be non-naturally occurring (i.e., non-native). Thus, in one embodiment a gene encoding a heterologous glycoprotein or glycopeptide is expressed from a nucleic acid construct. In other embodiments the gene encoding a heterologous glycoprotein or glycopeptide is integrated into the chromosome of the cell. The gene can also include regulatory sequences, for example a promoter and terminator, and can be inducible. The regulatory sequences can be heterologous or natural regulatory sequences in the cell. Inducible promoters may activate or increase transcription in response to an inducing agent. In contrast, the rate of transcription of a gene under control of a constitutive promoter is not dependent on an inducing agent. A constitutive promoter can be made a conditional or inducible promoter by the addition of sequences that confer responsiveness to particular conditions or to an inducing agent, as known in the art. Thus, promoters may be constitutive or may be inducible or conditional. Promoters or portions of promoters may also be combined in series to achieve a stronger level of expression or a more complex pattern of regulation, as known in the art.

The term "expression cassette" as used herein, refers to a nucleic acid construct that encodes a functional protein or functional RNA operably linked to expression control elements, such as a promoter, and optionally, any or a combination of other nucleic acid sequences that affect the transcription or translation of the gene, such as, but not limited to, a transcriptional terminator, a ribosome binding site, a splice site or splicing recognition sequence, an intron, an enhancer, a polyadenylation signal, an internal ribosome entry site, etc. The present invention provides numerous examples of expression cassettes useful for producing the cells and proteins of the invention, and for use in the methods of the invention. The expression cassettes can be comprised in any construct operable in the host cells being utilized. Generally an expression cassette will comprise a promoter, an open reading frame (ORF) encoding the heterologous protein of interest, and a terminator. Additional features can include 3' and 5' homology arms from genomic DNA of the host cell. These can be useful for inserting or integrating the expression cassette at a specific locus in the genome of the cell. Any of the components or features of the expression cassette can be active in any of the host cells described herein.

As used herein, "exogenous" with respect to a nucleic acid or gene indicates that the nucleic or gene has been introduced ("transformed") into an organism, microorganism, or cell by human intervention. Typically, such an exogenous nucleic acid is introduced into a cell or organism via a recombinant nucleic acid construct. An exogenous nucleic acid can be a sequence from one species introduced into another species, i.e., a heterologous nucleic acid. An exogenous nucleic acid can also be a sequence that is homologous to an organism (i.e., the nucleic acid sequence occurs naturally in that species or encodes a polypeptide that occurs naturally in the host species) that has been isolated and subsequently reintroduced into cells of that organism. An exogenous nucleic acid that includes a homologous sequence can often be distinguished from the naturally-occurring sequence by the presence of non-natural sequences linked to the exogenous nucleic acid, e.g., non-native regulatory sequences flanking the homologous gene sequence in a recombinant nucleic acid construct. Alternatively or in addition, a stably transformed exogenous nucleic acid can be detected and/or distinguished from a native gene by its juxtaposition to sequences in the genome where it has integrated. Further, a nucleic acid is considered exogenous if it has been introduced into a progenitor of the cell, organism, or strain under consideration.

As used herein, "expression" refers to the process of converting genetic information of a polynucleotide into RNA through transcription, which is typically catalyzed by an enzyme, RNA polymerase, and, where the RNA encodes a polypeptide, into protein, through translation of mRNA on ribosomes to produce the encoded protein.

The term "gene" is used broadly to refer to any segment of nucleic acid molecule that encodes a protein or that can be transcribed into a functional RNA. Genes may include sequences that are transcribed but are not part of a final, mature, and/or functional RNA transcript, and genes that encode proteins may further comprise sequences that are transcribed but not translated, for example, 5' untranslated regions, 3' untranslated regions, introns, etc. Further, genes may optionally further comprise regulatory sequences required for their expression, and such sequences may be, for example, sequences that are not transcribed or translated. Genes can be obtained from a variety of sources, including cloning from a source of interest or synthesizing from known or predicted sequence information, and may include sequences designed to have desired parameters.

The term "heterologous" when used in reference to a polynucleotide, a gene, a nucleic acid, a polypeptide, a protein, or an enzyme, refers to a polynucleotide, gene, a nucleic acid, polypeptide, protein, or an enzyme that is not derived from the host species. For example, "heterologous gene" or "heterologous nucleic acid sequence" as used herein, refers to a gene or nucleic acid sequence from a different species than the species of the host organism it is introduced into. Heterologous sequences can also be synthetic and not derived from the host species. When referring to a gene regulatory sequence or to an auxiliary nucleic acid sequence used for manipulating expression of a gene sequence (e.g. a 5' untranslated region, 3' untranslated region, poly A addition sequence, intron sequence, splice site, ribosome binding site, internal ribosome entry sequence, genome homology region, recombination site, etc.) or to a nucleic acid sequence encoding a protein domain or protein localization sequence, "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a genome, chromosome or episome. Thus, a promoter operably linked to a gene to which it is not operably linked to in its natural state (for example, in the genome of a non-genetically engineered organism) is referred to herein as a "heterologous promoter," even though the promoter may be derived from the same species (or, in some cases, the same organism) as the gene to which it is linked. Similarly, when referring to a protein localization sequence or protein domain of an engineered protein, "heterologous" means that the localization sequence or protein domain is derived from a protein different from that into which it is incorporated by genetic engineering.

The term "native" is used herein to refer to nucleic acid sequences or amino acid sequences as they naturally occur in the host. The term "non-native" is used herein to refer to nucleic acid sequences or amino acid sequences that do not occur naturally in the host, or are not configured as they are naturally configured in the host. A nucleic acid sequence or amino acid sequence that has been removed from a host cell, subjected to laboratory manipulation, and introduced or reintroduced into a host cell is considered "non-native." Synthetic or partially synthetic genes introduced into a host cell are "non-native." Non-native genes further include genes endogenous to the host microorganism operably linked to one or more heterologous regulatory sequences that have been recombined into the host genome, or genes endogenous to the host organism that are in a locus of the genome other than that where they naturally occur.

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. Nucleic acid molecules can have any three-dimensional structure. A nucleic acid molecule can be double-stranded or single-stranded (e.g., a sense strand or an antisense strand). Non-limiting examples of nucleic acid molecules include genes, gene fragments, exons, introns, messenger RNA (mRNA), transfer RNA, ribosomal RNA, siRNA, micro-RNA, tracrRNAs, crRNAs, guide RNAs, ribozymes, cDNA, recombinant polynucleotides, branched polynucleotides, nucleic acid probes and nucleic acid primers. A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

The nucleic acid molecules of the present disclosure will preferably be "biologically active" with respect to either a structural attribute, such as the capacity of a nucleic acid molecule to hybridize to another nucleic acid molecule, or the ability of a nucleic acid sequence to be recognized and bound by a transcription factor (or to compete with another nucleic acid molecule for such binding).

Nucleic acid molecules of the present disclosure include nucleic acid sequences of any length, including nucleic acid molecules that are preferably between about 0.05 kb and about 300 kb, or for example between about 0.05 kb and about 250 kb, or between about 0.05 kb and about 150 kb, or between about 0.1 kb and about 150 kb, or for example between about 0.2 kb and about 150 kb, about 0.5 kb and about 150 kb, or about 1 kb and about 150 kb.

The term "operably linked", as used herein, denotes a functional linkage between two or more sequences. For example, an operable linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous. Further, when used to refer to the joining of two protein coding regions, by "operably linked" is intended that the coding regions are in the same reading frame.

The terms "promoter", "promoter region", or "promoter sequence" refer to a nucleic acid sequence capable of binding RNA polymerase to initiate transcription of a gene in a 5' to 3' ("downstream") direction. A gene is "under the control of" or "regulated by" a promoter when the binding of RNA polymerase to the promoter is the proximate cause of said gene's transcription. The promoter or promoter region typically provides a recognition site for RNA polymerase and other factors necessary for proper initiation of transcription. A promoter may be isolated from the 5' untranslated region (5' UTR) of a genomic copy of a gene. Alternatively, a promoter may be synthetically produced or designed by altering known DNA elements. Also considered are chimeric promoters that combine sequences of one promoter with sequences of another promoter. Promoters may be defined by their expression pattern based on, for example, metabolic, environmental, or developmental conditions. A promoter can be used as a regulatory element for modulating expression of an operably linked polynucleotide molecule such as, for example, a coding sequence of a polypeptide or a functional RNA sequence. Promoters may contain, in addition to sequences recognized by RNA polymerase and, preferably, other transcription factors, regulatory sequence elements such as cis-elements or enhancer domains that affect the transcription of operably linked genes. A "Labyrinthulomycetes promoter" as used herein refers to a native or non-native promoter that is functional in Labyrinthulomycetes cells.

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. A recombinant cell contains a recombinant nucleic acid.

When applied to organisms, the terms "transgenic" "transformed" or "recombinant" or "engineered" or "genetically engineered" refer to organisms that have been manipulated by introduction of an exogenous or recombinant nucleic acid sequence into the organism. Non-limiting examples of such manipulations include gene knockouts, targeted mutations and gene replacement, promoter replacement, deletion, or insertion, as well as introduction of transgenes into the organism. For example, a transgenic microorganism can include an introduced exogenous regulatory sequence operably linked to an endogenous gene of the transgenic microorganism. Recombinant or genetically engineered organisms can also be organisms into which constructs for gene "knock down" have been introduced. Such constructs include, but are not limited to, RNAi, microRNA, shRNA, antisense, and ribozyme constructs. Also included are organisms whose genomes have been altered by the activity of meganucleases or zinc finger nucleases. A heterologous or recombinant nucleic acid molecule can be integrated into a genetically engineered/recombinant organism's genome or, in other instances, not integrated into a recombinant/genetically engineered organism's genome. As used herein, "recombinant microorganism" or "recombinant host cell" includes progeny or derivatives of the recombinant microorganisms of the disclosure. Because certain modifications may occur in succeeding generations from either mutation or environmental influences, such progeny or derivatives may not, in fact, be identical to the parent cell, but are still included within the scope of the term as used herein.

"Regulatory sequence", "regulatory element", or "regulatory element sequence" refers to a nucleotide sequence located upstream (5'), within, or downstream (3') of a polypeptide-encoding sequence or functional RNA-encoding sequence. Transcription of the polypeptide-encoding sequence or functional RNA-encoding sequence and/or translation of an RNA molecule resulting from transcription of the coding sequence are typically affected by the presence or absence of the regulatory sequence. These regulatory element sequences may comprise promoters, cis-elements, enhancers, terminators, or introns. Regulatory elements may be isolated or identified from untranslated regions (UTRs) from a particular polynucleotide sequence. Any of the regulatory elements described herein may be present in a chimeric or hybrid regulatory expression element. Any of the regulatory elements described herein may be present in a recombinant construct of the present disclosure.

The term "terminator" or "terminator sequence" or "transcription terminator", as used herein, refers to a regulatory section of genetic sequence that causes RNA polymerase to cease transcription.

The term "transformation", "transfection", and "transduction", as used interchangeably herein, refers to the introduction of one or more exogenous nucleic acid sequences into a host cell or organism by using one or more physical, chemical, or biological methods. Physical and chemical methods of transformation include, by way of non-limiting example, electroporation and liposome delivery. Biological methods of transformation include transfer of DNA using engineered viruses or microbes (for example, *Agrobacterium*).

Genetic Modifications

In some embodiments the cells of the invention comprise a genetic modification that causes a change in the N-glycan profile of glycoproteins or glycopeptides produced by the cell. In any of the embodiments herein the genetic modification can be a gene knockout, a deletion, a disruption, a mutation (e.g. a point mutation), a rearrangement, a replacement, a suppressor mutation, a targeted mutation, a replacement, a mis-sense mutation, a deletional insertion, a substitution, or an insertion, any of which can be in combination with the introduction of heterologous genes into the organism. In some embodiments the genetic modification is done on a gene that encodes a mannosyl transferase. In some embodiments the gene can encode an enzyme of the class EC 2.4.1.258, which are alpha 1,3-mannosyl transferases. These enzymes catalyze the first ER luminal step of N-linked glycosylation as illustrated in FIG. 2. In other embodiments the gene can encode an alpha-3,3-mannosyl transferase. A gene is considered deleted, disrupted, inactivated, or knocked out when it is either no longer expressed, or has been modified so that it no longer produces a product providing the function of the product of the natural gene. In another embodiment the modification can result in a functional reduction of activity in a particular gene, such as a mannosyl transferase as described herein. By functional reduction of activity is meant that the activity of the enzyme encoded by the gene is reduced, and the reduction can be due to a change in the sequence of the encoded gene (i.e. a mutation of one or more genes). The functional reduction of activity of one or more mannosyl transferase genes can also be performed by performing a genetic modification in a regulatory sequence (e.g. a promoter) for one or more mannosyl transferase genes, which thus causes a functional reduction in mannosyl transferase activity, for example by inhibiting transcription or expression of the gene(s). The genetic modification of the regulatory sequence can be any of the same modifications described herein, for example a mutation, deletion, disruption or other modification of one or more promoters controlling expression of one or more mannosyl transferase gene(s).

Mannosyl Transferase Family

The mannosyl transferase genes modified in the invention can be an alpha-1,2-mannosyl transferase, or an alpha-1,3-mannosyltransferase, or an alpha-1,6-mannosyltransferase. In some embodiments the cells and methods of the invention comprise a genetic modification (e.g. a deletion, knock out, disruption, or other genetic modification described herein) to one or more gene(s) that is/are a member of the mannosyl transferase gene family. Members of this family include, but are not limited to, Alg1, Alg2, Alg3, Alg6, Alg8, Alg9, Alg10, Alg11, Alg13, and Alg14. The genetic modification can be present in any one or more of the mannosyl transferase genes. These genes can be present as more than one copy and the cells and methods can have the genetic modification to all copies of the gene. In one embodiment the deletion, disruption, or other genetic modification is to one or more Alg3 gene(s), which encodes an enzyme that catalyzes the addition of the first dol-P-Man derived mannose in an alpha-1,3 linkage to Man5GlcNAc$_2$-PP-Dol. Genes that are members of the Alg3 sub-family encode an alpha-1,3-mannosyl transferase and are found in fungi, mammals, yeast, Labyrinthulomycetes (e.g. family Thraustochytriaceae, including but not limited to *Schizochytrium, Aurantiochytrium, Thraustochytrium*), and other Labyrinthulomycetes), and a wide variety of other organisms. In a specific embodiment the modification is a deletion or knock out or disruption of one or more Alg3 gene(s), which can be done in a host cell that is a member of the family Thraustochytriaceae. e.g. *Schizochytrium* or *Aurantiochytrium*. Some cells contain more than one Alg3 gene and the deletion, knock out, or disruption can be in any one or more of the Alg3 genes, or all of the Alg3 genes.

It was discovered that the deletion, disruption, or knock out of Alg3 in a organism of the family Thraustochytriaceae (e.g. an *Aurantiochytrium, Schizochytrium*, or *Thraustochytrium*) resulted in production of a glycosylated protein or peptide having an N-glycan profile that was simplified or humanized, e.g. having high amounts of Man3 and/or Man4 structure described herein.

Glycoproteins and glycopeptides have one or more carbohydrate groups attached to their polypeptide chain. In some embodiments the glycoprotein or glycopeptide produced by the cells of the invention can be a therapeutic protein or peptide, e.g. enzymes, Ig-Fc-Fusion proteins, or an antibody. The antibody can be a functional antibody or a functional fragment of an antibody. In various embodiments the antibody can be alemtuzumab, denosumab, eculizumab, natalizumab, cetuximab, omalizumab, ustekinumab, panitumumab, trastuzumab, belimumab, palivizumab, natalizumab, abciximab, basiliximab, daclizumab, adalimumab (anti-TNF-alpha antibody), tositumomab-1131, muromonab-CD3, canakinumab, infliximab, daclizumab, tocilizumab, thymocyte globulin, anti-thymocyte globulin, or a functional fragment of any of them. The glycoprotein can also be alefacept, rilonacept, etanercept, belatacept, abatacept, follitropin-beta, or a functional fragment of any of them. The antibody can also be any anti-TNF-alpha antibody or an anti-HER2 antibody, or a functional fragment of any of them. The glycoprotein can be an enzyme, for example idursulfase, alteplase, laronidase, imiglucerase, agalsidase-beta, hyaluronidase, alglucosidase-alpha, GalNAc 4-sulfatase, pancrelipase, DNase. In various embodiments the glycoprotein or glycopeptide can be of a size of up to 100 kDa or up to 200 kDa or up to 300 kDa or up to 500 kDa or up to 750 kDa. When a glycopeptide it can have at least 10 or at least 15 or at least 20 amino acids. The glycoprotein or glycopeptide can be an antibody and a therapeutic protein, as well as a monoclonal antibody. A functional antibody or antibody fragment is a molecule that is an antibody or antibody fragment that binds to a target epitope and thereby produces a desired response, for example a biological response or action, or the cessation of a response or action). The desired response can be the same as the response to a natural antibody, but the response can also be to mimic or disrupt the natural biological effects associated with ligand-receptor interactions.

When the protein is a functional fragment of an antibody it can comprise at least a portion of the variable region of the heavy chain, or can comprise the entire antigen recognition unit of an antibody, hut nevertheless comprise a sufficient portion of the complete antibody to perform the antigen binding properties that are similar to or the same in nature and affinity to those of the complete antibodies. In various embodiments a functional fragment of a glycoprotein, glycopeptide, glycolipid, antibody, or immunoglobulin can comprise at least 10% or at least 20% or at least 30% or at least 50% or at least 60% or at least 70% or at least 80% or at least 90% or at least 95% of the native sequence, and optionally can also have at least 70% or at least 80% or at least 90% or at least 95% sequence identity to that indicated portion of the native sequence; for example, a functional fragment can comprise at least 85% of the native antibody sequence, and have a sequence identity of at least 90% to that portion of the native antibody sequence. Any of the recombinant cells disclosed herein can comprise a nucleic acid encoding a functional and/or assembled antibody molecule described herein, or a functional fragment thereof.

Any of the recombinant cells disclosed herein can comprise a nucleic acid encoding a functional and/or assembled antibody molecule described herein, or a functional fragment thereof. In various embodiments the therapeutic peptide can be hormones, human growth hormone, lecutinizing hormone, thyrotropin-alpha, interferon, darbepoetin, erythropoietin, epoetin-alpha, epoetin-beta, FS factor VIII, Factor VIIa, Factor IX, anithrombin/ATIIcytokines, clotting factors, insulin, erythropoietin (EPO), glucagon, glucose-dependent insulinotropic peptide (GIP), cholecystokinin B, enkephalins, and glucagon-like peptide (GLP-2) PYY, leptin, and antimicrobial peptides.

Promoters and Terminators

The recombinant cell or organism of the invention can be any suitable organism but in some embodiments is a Labyrinthulomycetes cell, and the promoter (and terminator) can be any suitable promoter and/or terminator. Promoters and/or terminators can be used in any combination. For example, any promoter described herein or other promoters that may be isolated from or functional in Labyrinthulomycetes or derived from such sequences can be used in combination with any terminator described herein or other terminators functional in the recombinant cell or organism, or derived from such sequences. For example, terminator sequences may be derived from organisms including, but not limited to, heterokonts (including Labyrinthulomycetes, fungi, algae, microalgae, and other eukaryotic organisms. In various embodiments the promoter and/or terminator is any one operable in a cell or organism that is a Labyrinthulomycetes, including any genus thereof. Any of the constructs can also contain one or more selection markers, as appropriate. A large number of promoters and terminators can be used with the host cells of the invention. Those described herein are examples and the person of ordinary skill with resort to this disclosure will realize or be able to identify other promoters useful in the invention. Examples of promoters include the alpha-tubulin promoter, the TEFp promoter, Hsp60-788 promoter, Tsp-749 promoter, Tubα738 promoter, Tubα-997 promoter, a promoter from the polyketide synthase system, and a fatty acid desaturase promoter. Examples of useful terminators include pgk1, CYC1, and eno2. Promoters and terminators can be used in any advantageous combination and all possible combinations of promoters and terminators are disclosed as if set forth fully herein.

In some embodiments the expression cassettes of the invention comprise one or more of 1) one or more signal sequences; 2) one or more promoters; 3) one or more terminators; and 4) an exogenous sequence encoding one or more proteins, which can be a heterologous protein; 4) optionally, one or more selectable markers for screening on a medium or a series of media. These components of an expression cassette can be present in any combination, and each possible sub-combination is disclosed as if fully set forth herein. In specific embodiments the signal sequences can be any described herein, but can also be other signal sequences. Various signal sequences for a variety of host cells are known in the art, and others can be identified with reference to the present disclosure and which are also functional in the host cells. In exemplary specific embodiments the promoter can be an alpha-tubulin promoter or TEFp, with alpha-tubulin promoter being the weaker of the two. The promoters can be paired with any suitable terminator, but in specific embodiments the tubαp can be paired with the pgk1t terminator. In another embodiment the TEFp promoter can be paired with the eno2 terminator, both terminators being from *Saccharomyces cerevisiae* and also being functional in Labyrinthulomycetes. The selectable marker can be any suitable selectable marker or markers but in specific embodiments it can be nptII or hph. In one embodiment nptII can be linked to the heavy chain constructs and hph can be linked to the light chain constructs.

The present invention also provides a nucleic acid construct or disruption cassette for performing a deletion, knock out, or disruption in a gene that encodes a mannosyl transferase. The nucleic acid construct can be regulated by a promoter sequence and, optionally, a terminal sequence functional in a host cell. The host cell can comprise an expression cassette and also a deletion, knock out, or disruption cassette as disclosed herein, which can also be a CRISPR/Cas 9 cassette that can delete any one or more of the target genes as disclosed herein. In any of the embodiments the host cell can be a Labyrinthulomycetes, such as a cell of the family Thraustochytriaceae (e.g. an *Aurantiochytrium*, a *Schizochytrium*, or a *Thraustochytrium*). The construct or cassette can also have a sequence encoding 5' and 3' homology arms to the gene encoding a mannosyl transferase, such as a 1,3-mannosyl transferase (e.g., one or more Alg3 genes). The construct can also have a selection marker, which in one embodiment can be nat, but any appropriate selection marker can be used.

Methods

The invention also provides methods of producing heterologous glycoproteins and glycopeptides in host cells (e.g. Labyrinthulomycetes cells) that have an N-glycan profile described herein. The methods can involve any one or more steps of: transforming a host cell with an expression vector or linear nucleic acid encoding a heterologous glycoprotein or glycopeptide for expression from the vector or integration into the chromosome of the cell; a step of a transforming the host cell with a deletion, knock out, or disruption cassette, which can be directed to a gene enocoding a mannosyl transferase enzyme (e.g. alg3); a step of deleting or knocking out or disrupting one or more gene(s) that encodes a mannosyl transferase, as disclosed herein; cultivating the cell; and harvesting a glycoprotein or glycopeptide that has an N-glycan profile described herein. The host cell can be any described herein.

The invention also provides methods of producing a glycoprotein or glycopeptide described herein. The methods involve providing a recombinant Labyrinthulomycete cell that produces a heterologous glycoprotein or glycopeptide; and wherein the cell produces and expresses a mannosyl transferase enzyme; and contacting the recombinant cell with a molecule that reduces mannosyl transferase enzyme activity in the cell to thereby produce the glycoprotein or glycopeptide having an N-glycan profile described herein. The N-glycan profile of the glycoprotein or glycopeptide produced can be any as described herein.

The invention also provides a method of producing a glycoprotein or glycopeptide having an N-glycan profile, such as any disclosed herein. The method involves providing a recombinant Labyrinthulomycete cell described herein that produces a heterologous glycoprotein or glycopeptide, modifying the Labyrinthulomycete cell to reduce or inactivate at least one mannosyl transferase enzyme of the cell, and producing the glycoprotein or glycopeptide. Modifying the cell can involve disrupting or deleting a gene encoding the mannosyl transferase enzyme. In various embodiments the cell is modified by inactivating the transcription or translation of a gene encoding one or more mannosyl transferase enzyme(s), or by contacting the Labyrinthomycete cell with an inhibitor of mannosyl transferase. In another embodiment the mannosyl transferase enzyme can be inactivated by contacting the enzyme with antisense RNA, RNAi, or a ribozyme. The one or more mannosyl transferase enzyme(s) can also be inactivated by a transcriptional regulator. The inhibitor can be produced by one or more nucleic acid molecules comprised in the cell or by any method described herein. And the inhibitor can be any described herein.

Enzyme Inhibition

In some embodiments the activity of the mannosyl transferase can be inhibited, reduced, or eliminated through the use of RNA interference (RNAi) to inhibit the expression of one or more genes encoding a mannosyl transferase. The mannosyl transferase inhibited can be any as described herein or can be a separate gene that, when expressed, binds to the enzyme or otherwise causes a reduction in activity of the enzyme. The RNAi suppression of a gene can be accomplished by methods known in the art including, but not limited to, the use of antisense RNA, a ribozyme, small interfering RNA (siRNA) or microRNA (miRNA). The siRNA or miRNA can be transcribed from a nucleic acid inserted into the genome of the cell, or can be transcribed from a plasmid or other vector transformed into the cell, or can be provided in a growth medium in which the cell is comprised.

In other embodiments the activity of the mannosyl transferase enzyme can be inhibited by the use of an enzyme inhibitor. The inhibitor can be a glycosylation inhibitor, and can be an inhibitor of mannosyl transferase or another enzyme in the glysosylation pathway. In various embodiments the inhibitor can be rhodamine-3-acetic acid or 5-[[3-(1-phenylethoxy)-4-(2-phenylethoxy)phenyl]methylene]-4-oxo-2-thioxo-3-thiazolidineacetic acid (5a). In other embodiments the inhibitor can be a protein or peptide inhibitor. In other embodiments the inhibitor can be brefeldin A, 6-diazo-5-oxo-L-norleucine, fructose-6-phosphate amidotransferase, chlorate, 2-deoxyglucose, 3-deoxy-3-fluoroglucosamine, 4-deoxy-4-fluoroglucosamine, 2-deoxy-2-fluoroglucose, 2-deoxy-2-fluoromannose, a plant alkaloid (e.g. castanospermine, australine, deoxynojirimycin, swainsonine, or alkylated or acetlated analogs of them). Persons of ordinary skill with resort to this disclosure will realize additional inhibitors that are useful in the invention. The enzyme inhibitors can be produced by nucleic acids inserted into the genome of the cell, or can be produced from nucleic acids present on a plasmid or other vector transformed into the cell, or can be included in a growth medium in which the cell is grown. The inhibitor can also be an antibody directed to one or more epitopes on the enzyme, or on a substrate for the enzyme.

Compositions

The present invention also provides compositions having a glycoprotein or glycopeptide that has a humanized or simplified N-glycan profile (or N-glycan profile) as described herein and is derived from a recombinant Labyrinthulomycete cell described herein. Derived from a cell means that the glycoprotein or glycopeptide was synthesized by the cell. In some embodiments the entire glycoprotein or glycopeptide was synthesized by the cell, including the glycan portion. In some embodiments the glycoprotein or glycopeptide synthesized by the cell comprises more than 25% or more than 50% or more than 75% or all of the glycoprotein or glycopeptide in the composition. The cell can comprise a genetic modification in a gene that encodes a mannosyl transferase, as described herein. In one embodiment the genetic modification is a deletion in an alg family gene, such as alg3. The composition can be any of the compositions derived from host cells, as described herein.

Example 1-Trastuzumab Expression Constructs: pCAB056, 057, 060, 061

This example discloses specific expression constructs that can be applied in the present invention, but persons of ordinary skill with resort to this disclosure will realize many other constructs and variations of those here that can be utilized. Specific constructs pCAB056, 057, 060, and 061 are described in Table 1, which are disclosed with signal peptides. While specific signal peptides are provided herein other signal peptide can be utilized in the invention.

Construct pCAB056 contains the trastuzumab (or HERCEPTIN®) light chain with SEQ ID NO: 1, a signal peptide (#552), expressed from the TEF promoter. This cassette also carries a marker (hph) encoding resistance to hygromycin B. Construct pCAB057 contains the trastuzumab light chain with SEQ ID NO: 2, a signal peptide (#579), expressed from the TEF promoter. This cassette also carries a marker (hph) encoding resistance to hygromycin B. Construct pCAB060 contains the trastuzumab heavy chain with, a signal peptide (#552), expressed from the TEF promoter. This cassette also carries a marker (nptII) encoding resistance to paromomycin. Construct pCAB061 contains the trastuzumab heavy chain with a signal peptide (#579) expressed from the TEF promoter. This cassette also carries a marker (nptII) encoding resistance to paromomycin. In view of this disclosure the constructs can be synthesized through ordinary means. In other embodiments the constructs can use other promoters, as described herein. Examples of useful terminators include pgk1, CYC1, and eno2, any of which can be paired with other markers.

TABLE 1

Summary of trastuzumab expression constructs

| Construct | Promoter | Signal peptide | Gene | Marker |
|---|---|---|---|---|
| pCAB056 | TEF | SP552 SEQ ID NO: 1 | trastuzumab light chain | hph |
| pCAB057 | TEF | SP579 SEQ ID NO: 2 | trastuzumab light chain | hph |
| pCAB060 | TEF | SP552 | trastuzumab heavy chain | nptII |
| pCAB061 | TEF | SP579 | trastuzumab heavy chain | nptII |

Example 2-Construction of Trastuzumab-Producing Strains (5942, 5950. And 5951)

Trastuzumab (HERCEPTIN®) was produced by co-transforming a wild type *Aurantiochytrium* cell #6267 with a pool of DNA comprised of linearized versions of pCAB056, 057, 060 and 061 from Example 1. Transformants that were resistant to both hygromycin B and paromomycin were screened by ELISA for production of antibody. Each clone was cultured overnight in 3 ml FM2 (17 g/L sea salt, 10 g/L yeast extract, 10 g/L peptone, 20 g/L dextrose) in a 24-well plate. They were then diluted 1000× into fresh FM2 (3 mL) and incubated for about 24 hours. The cells were pelleted by centrifugation and the supernatants were assayed using a heavy chain capture/light chain detect sandwich ELISA. The transformants were also screened by colony PCR to determine which signal peptides were present in the top producing clones. The strains with the 3 highest trastuzumab titers measured by sandwich ELISA are shown in Table 2. Diagnostic PCR revealed which signal peptides were linked to the heavy and light chains present in these strains (Table 2). All of the clones were found to have both the heavy and light chains linked to SEQ ID NO: 2 (SP #579) with one exception; Her.2.24 was found to have heavy chains with both SEQ ID NO: 1 (SP #552) and SEQ ID NO: 2 (SP #579).

TABLE 2

Trastuzumab titers and signal peptides in top clones

| Clone # | strain ID# | Signal peptide on light chain | Signal peptide on heavy chain | Titers (mg/L) |
|---|---|---|---|---|
| Her.1.2 | #5942 | 579 | 579 | 30 |
| Her.2.24 | #5950 | 579 | 552, 579 | 16 |

Example 3-Construction of Alg3 Deletion Cassettes

This example describes the construction of a linear fragment of DNA for the disruption of the alg3 gene. Three Alg3 genes identified as SG4EUKT579099 (SEQ ID NO: 3), SG4EUKT579102 (SEQ ID NO: 4), and SG4EUKT561246 (SEQ ID NO: 5) were found in the genome assembly of the wt *Aurantiochytrium* sp. All three sequences encode a 434 amino acid protein. SG4EUKT579099 and SG4EUKT579102 are identical at both the amino acid and nucleotide levels. SG4EUKT561246 has more than 99% identity to the other sequences at both the amino acid and nucleotide levels. This high level of identity allowed for the deletion of all three sequences with a single disruption cassette (alg3::nat) comprised of a selectable marker (nat) (which provides resistance to nourseothricin) flanked by 5' and 3' alg3 homology arms. The alg3::nat disruption cassette was generated by amplifying the 5' and 3' alg3 homology arms from a wild type strain genomic DNA, while the selectable marker (nat) was amplified from nat containing plasmid DNA.

Example 4—Deletion of Alg3

A trastuzumab-producing strain was transformed with the linear alg3::nat disruption cassette described in Example 3. Nourseothricin-resistant colonies were screened for the deletion of alg3 by quantitative PCR (qPCR). Four clones were identified that had Alg3 deleted and these clones were given strain IDs: #6667, #6668, #6669, and #6670.

Example 5—Antibody Production in 24 Well Plates

The alg3 deletion clones described in Example 4 were cultivated in 24 well plates for 22 hours and the trastuzumab levels in the supernatant were determined by ELISA. The results are shown in Table 3.

TABLE 3

Trastuzumab titers in small scale cultures of alg3 deleted clones.

| Strain ID | Trastuzumab titers (mg/L) |
|---|---|
| #6667 | 6.9 |
| #6668 | 7.5 |
| #6669 | 7.0 |
| #6670 | 9.8 |

Example 6—Fermentation of Alg3+ Strain and Alg3− Deletion Strain

A 2-liter fermenter containing a medium (Table 4) comprised of yeast extract, peptone, salts, and glucose is inoculated with cells from a shake flask culture grown in a comparable medium. The production fermentation has a growth phase to increase cell density and produce the antibody. The production fermenter is operated until the culture reaches a biomass concentration between 50 to 100 g wet cell weight/L. A concentrated dextrose feed (Table 5) is started once the dextrose concentration reaches less than 5 g/L and henceforth, the dextrose concentration is kept below 1 g/L. The pH is maintained at 6.0 using 30% ammonium hydroxide or ammonia (pure gas). FIGS. 3A and 3B show the production of antibody (mg/L), biomass (g dry cell weight/L) and total FAME (g/L) produced by the fermentation that employed #5942 and #6670, respectively. This results are consistent with those from Example 3 as they clearly show that deletion of alg3 did not have a deleterious effect on antibody titers in 2 L fermentation.

TABLE 4

Production Medium Composition

| Medium Components | Concentration | Unit |
|---|---|---|
| Sodium Chloride (NaCl) | 0 to 24 | g/L |
| Calcium Chloride (CaCl$_2$) | 0 to 0.8 | g/L |
| Sodium Sulfate (Na$_2$SO$_4$) | 0 to 20 | g/L |
| Potassium Phosphate (KH$_2$PO$_4$) | 1 to 10 | g/L |
| Ammonium sulfate ((NH$_4$)$_2$SO$_4$) | 0 to 5 | g/L |
| Potassium Chloride (KCl) | 0 to 10 | g/L |
| Yeast Extract (Tastone 154) | 0 to 100 | g/L |
| Peptone BD | 0 to 100 | g/L |
| Magnesium Sulfate (MgSO$_4$•7H$_2$O) | 0 to 10 | g/L |
| Sodium EDTA-2H20 (Na$_2$EDTA•2H$_2$O) | 0 to 500 | mg/L |
| Boric Acid (H$_2$BO$_3$) | 0 to 500 | mg/L |
| Iron Chloride (FeCl$_2$•4H$_2$O) | 0 to 500 | mg/L |
| Cobalt Chloride (CoCl$_2$•6H$_2$O) | 0 to 500 | mg/L |
| Manganese Chloride (MnCl$_2$•4H$_2$O) | 0 to 1000 | µg/L |
| Zinc Chloride (ZnCl$_2$) | 0 to 1000 | µg/L |
| Nickel Sulfate (NiSO$_4$•6H$_2$O) | 0 to 1000 | µg/L |
| Copper Sulfate (CuSO$_4$•5H$_2$O) | 0 to 1000 | µg/L |
| Sodium Molybdenate (Na$_2$MoO$_4$•2H$_2$O) | 0 to 1000 | µg/L |
| Vitamin B12 | 0 to 1000 | µg/L |
| Biotin | 0 to 1000 | µg/L |
| Thiamine | 0 to 5000 | µg/L |

TABLE 5

Feed Composition for Production Fermentation

| Feed components | Concentration | Unit |
|---|---|---|
| Dextrose | 0 to 900 | g/L |
| Magnesium Sulfate (MgSO$_4$•7H$_2$O) | 0 to 50.0 | g/L |
| Yeast Extract (Tastone 154) | 0 to 100 | g/L |
| Peptone BD | 0 to 100 | g/L |
| Ammonium Sulfate ((NH$_4$)$_2$SO$_4$) | 0 to 50.0 | g/L |
| Sodium EDTA-2H$_2$O (Na$_2$EDTA•2H$_2$O) | 0 to 500 | mg/L |
| Iron Chloride (FeCl$_2$•4H$_2$O) | 0 to 500 | mg/L |
| Manganese Chloride (MnCl$_2$•4H$_2$O) | 0 to 500 | mg/L |
| Boric Acid (H$_2$BO$_3$) | 0 to 500 | mg/L |
| Sodium Molybdenate (Na$_2$MoO$_4$•2H$_2$O) | 0 to 1000 | µg/L |
| Zinc Chloride (ZnCl$_2$) | 0 to 1000 | µg/L |
| Cobalt Chloride (CoCl$_2$•6H$_2$O) | 0 to 1000 | µg/L |
| Copper Sulfate (CuSO$_4$•5H$_2$O) | 0 to 1000 | µg/L |
| Nickel Sulfate (NiSO$_4$•6H$_2$O) | 0 to 1000 | µg/L |
| Vitamin B$_{12}$ (Cyanocobalamin) | 0 to 1000 | µg/L |
| Biotin | 0 to 1000 | µg/L |
| Thiamine | 0 to 5000 | µg/L |

Example 7-Purification of Antibody

The antibodies from the supernatants produced via fermentation were purified using 3 steps: 1) flocculation to remove cells and other insoluble material by centrifugation; 2) buffer exchange using tangential flow filtration (TFF); 3) protein A capture and release chromatography.

Cell supernatants were mixed with 5 M NaCl and polyethyleneimine (PEI) to a final concentration of 0.2% w/v PEI and 0.3 M of additional NaCl. After mixing for 5 minutes at room temperature the solution was centrifuged at 5,250×g for 15 min at 4° C., followed by an additional centrifugation at 18,000 g for 20 min at 4° C. The supernatant was then subjected to TFF buffer exchange by passing 3 volumes of protein A binding buffer (20 mM sodium phosphate pH 7.0) through a 30,000 MWCO crossflow cassette. The recovered solution was filtered through a 0.45 µm cellulose acetate filter. The antibody was captured with a pre-equilibrated Protein A column. Non-specific bound proteins were removed from the resin by washing with 40 mL of biding buffer. The antibody was removed from the column using elution buffer (100 mM sodium citrate pH 3.0). Centrifugal columns were used to exchange buffers and formulate the antibody in phosphate buffered saline (PBS). Gel images for each of the purification steps are shown in FIG. 4. Antibody concentration was measured by the absorbance at 280 nm (extinction coefficient, e280=225,000 $M^{-1}cm^{-1}$); 34.4 mg and 53.6 mg of antibody were purified from the Alg3+ strain and Alg3− strain, respectively.

Example 8-Glycosilation Analyses

Purified antibodies produced by the Alg3+ and Alg3− strains were analyzed by release of glycans using PNGaseF and PNGaseA and analysis by MALDI TOF/TOF and ESI-MS. The analysis of all data give a complete picture of the number and abundance of all glycans present in each sample, as well as the structures in each sample.

The combined data from the previous analyses confirmed that N-linked glycosylation in both samples only occurred at the expected site, Asn327. There was no detectable O-glycosylation in either sample. A large number of high mannose glycans, some of which contained xylose and sulfated structures, were detected on antibody from Alg3+ strain; whereas far fewer N-linked glycans were observed on sample from Alg3− strain (FIGS. 4-5 and 7-8). None of the N-linked glycans produced by Alg3− contain xylose. The majority of the N-linked glycans produced by Alg3− have a Man3 structure (FIGS. 5, 7 and 8).

These analyses show there is a large difference in the glycan profile after alg3 deletion. With respect to paucimannose N-glycans, based on the method of glycan release, there are between 0 and 3% in the Alg3+ strain profile, while there are between 89 and 90% in the Alg3− strain profile. Similarly, with respect to high mannose N-glycans, based on the method of glycan release, there are between 97% and 100% in the Alg3+ strain profile, while there are between 10% and 11% in the Alg3− strain profile. Thus, the deletion of alg3 resulted in a reduction (up to 90%) in high mannose N-glycans and a simultaneous increase (up to 3000%) in the production of paucimannose N-glycans.

Table 6 below shows differences between alg3+ and alg3− strains with respect to high mannose and paucimannose N-glycan profiles. Note that the alg3− strains produced the heterologous glycoprotein in high amounts and free of any xylose, fucose, galactose, or other carbohydrate moieties attached to the Man3NAc2 and/or Man4NAc2 core.

TABLE 8

| Strain | N-glyans | % N-linked glycans | |
|---|---|---|---|
| | | PNGaseF | PNGaseA |
| #5942 | High mannose | 97 | 100 |
| #5942 | Pauci-mannose | 3 | 0 |
| #6670 | High mannose | 10 | 11 |
| #6670 | Pauci-mannose | 90 | 89 |

Although the disclosure has been described with reference to the above examples, it will be understood that modifications and variations are encompassed within the spirit and scope of the disclosure. Accordingly, the disclosure is limited only by the following claims.

The invention claimed is:

1. A recombinant cell of the family Thraustochytriaceae comprising:
   a nucleic acid molecule encoding a heterologous glycoprotein or glycopeptide;
   a genetic modification to one or more gene(s) encoding a mannosyl transferase,
   wherein the cell produces the heterologous glycoprotein or glycopeptide having an N-linked glycan profile comprising at least 50% paucimannose N-glycan structures.

2. The cell of claim 1 wherein the genetic modification is selected from the group consisting of: a deletion, an insertion, a replacement, and a disruption.

3. The cell of claim 1 wherein the genetic modification is a deletion and the mannosyl transferase is an alpha-1,3-mannosyl transferase.

4. The cell of claim 1 wherein the mannosyl transferase is of the class EC 2.4.1.258.

5. The cell of claim 1 wherein the heterologous glycoprotein or glycopeptide is an antibody.

6. The cell of claim 1 wherein the heterologous glycoprotein is selected from the group consisting of: trastuzumab, eculizumab, natalizumab, cetuximab, omalizumab, usteinumab, panitumumab, and adalimumab, or a functional fragment of any of them.

7. The cell of claim 3 wherein the heterologous glycoprotein or glycopeptide has an N-linked glycan profile having at least 50% fewer high mannose N-linked glycans than the N-linked glycan profile from a corresponding cell that does not comprise the mannosyl transferase deletion.

8. The cell of claim 1 wherein the glycoprotein or glycopeptide has an N-linked glycan profile having less than 20% high mannose structures.

9. The cell of claim 1 from a genus selected from the group consisting of: Aurantiochytrium, Schizochytrium, and Thraustochytrium.

10. The cell of claim 3 wherein the glycoprotein or glycopeptide comprises at least 25% fewer xylose moieties than the cell that does not comprise the mannosyl transferase deletion.

11. The cell of claim 3 wherein the cell is an Aurantiochytrium sp.

12. The cell of claim 10 wherein the glycoprotein or glycopeptide does not comprise N-linked glycans comprising xylose.

13. The cell of claim 1 wherein the N-linked glycans comprise at least 80% paucimannose structures.

14. The cell of claim 1 wherein N-linked glycans comprise at least 70% Man3.

15. The cell of claim 1 wherein the N-linked glycan profile comprises at least 70% fewer high mannose structures compared to a reference cell not comprising the genetic modification.

16. A method of producing a glycoprotein or glycopeptide that comprises a simplified N-glycan profile comprising:
   a. performing a genetic modification to a gene that encodes a mannosyl transferase in a Thraustochytriaceae host cell that comprises a nucleic acid that encodes a heterologous glycoprotein or glycopeptide;
   b. cultivating the host cell;
   c. harvesting the heterologous glycoprotein or glycopeptide from the cell that has an N-linked glycan profile comprising at least 50% paucimannose structures.

17. The method of claim 16 wherein the mannosyl transferase is an alpha-1,3-mannosyl transferase.

18. The method of claim 17 wherein the mannosyl transferase is of the class EC 2.4.1.258.

19. The method of claim 17 wherein the genetic modification is a deletion, and the glycoprotein or glycopeptide is an antibody.

20. The cell of claim 17 wherein the glycoprotein or glycopeptide is selected from the group consisting of: trastuzumab, eculizumab, natalizumab, cetuximab, omalizumab, usteinumab, panitumumab, and adalimumab, or a functional fragment of any of them.

21. The method of claim 16 wherein the glycoprotein or glycopeptide comprises at least 50% N-linked glycans that are paucimannose.

22. The method of claim 16 wherein the N-linked glycan profile comprises less than 25% high mannose structures.

23. The method of claim 16 wherein the Thraustochytriaceae cell is selected from the group consisting of: *Aurantiochytrium, Schizochytrium*, and *Thraustochytrium*.

24. The method of claim 16 wherein the glycoprotein or glycopeptide comprises at least 25% fewer xylose moieties than a reference cell that does not comprise the mannosyl transferase deletion.

25. The method of claim 23 wherein the Thraustochytriaceae cell is an *Aurantiochytrium* sp.

26. The method of claim 23 wherein the glycoprotein or glycopeptide does not comprise N-linked glycans comprising xylose.

27. The method of claim 16 wherein more than 75% of the N-linked glycans are paucimannose.

28. The method of claim 27 wherein the paucimannose structures comprise at least 30% Man3 structures.

\* \* \* \* \*

SEQUENCE LISTING

```
<160> NUMBER OF SEQ ID NOS: 5

<210> SEQ ID NO 1
<211> LENGTH: 30
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: #552, i1485, Schizochytrium sp

<400> SEQUENCE: 1

Met Lys Phe Ala Thr Ser Val Ala Ile Val Leu Val Ala Asn Val Ala
1               5                   10                  15

Thr Ala Leu Ala Gln Ser Asp Gly Cys Thr Ala Thr Asp Gln
            20                  25                  30

<210> SEQ ID NO 2
<211> LENGTH: 27
<212> TYPE: PRT
<213> ORGANISM: Artificial Sequence
<220> FEATURE:
<223> OTHER INFORMATION: Synthetic
```

<220> FEATURE:
<221> NAME/KEY: misc_feature
<223> OTHER INFORMATION: #579, Batrachochytrium dendrobatidis

<400> SEQUENCE: 2

Met Pro Phe Asn Arg Leu Ser Leu Pro Cys Leu Leu Leu Ala Leu Ile
1               5                   10                  15

Ala Ser Leu Phe Ile His Ala Ala Gln Ala Gly
            20                  25

<210> SEQ ID NO 3
<211> LENGTH: 1305
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SG4EUKT579099, Alg3.1 gene from
      Aurantiochytrium

<400> SEQUENCE: 3

```
atgtctttgc gtgcgagtaa ggatgccctc gtacgtcttc gaggggccct cgacaatgca      60
agcactcagt ggtggtggtg ggccatggca gccacggcag acttggcact tagcctgctt     120
attgtgaaac tcgtgcctta tacggagatc gactttaaag cgtacatgca agaggttgaa     180
ggcccctat tgcatgatga atgggactat acaaagctca ggggcgacac aggcccgctg      240
gtttatcctg ccggttttgt gtatatttat atgggcatcc gctggctcac tgaagacggc     300
acgaacctgt ggcgaggcca gatacttttt gcaagtctgc atgcaattct tgtttacctt     360
gtacttggat ccatatatta ccagccagat gcatcaaaag atcctcgcag agtgccgttc     420
tgggtaggac tctagcagt attatcgaga cgtgtgcatt caatctttgt tctgaggctc      480
ttcaacgacg gcattgctat ggtgtttatg tatgcagcag tatatatgta tgtgcggagg     540
cgttggacgc taggtacggc tttcttcagc gcagcactta gcgtgaaaat gaatatactc     600
ctatttgcgc caggattagc cgtgttgatg ctcgaggcta cgggtttggc gtcgagcata     660
ctgcaggcag tgatctgcgt agcatcacag attgccttag cttttgccgtt cctccaagtc   720
aacgcagccg ggtatctaaa tcgggctttt gagctaggtc gtgtctttac gtacaaatgg     780
acagtaaact tcaagtttct cagccctgaa gcttttgtga gtaaggcact tgcccaaggc     840
ctgctgtctg ccacttact tacatgggtc ggctttgggt ctcgccactt tgcttcctct      900
cacacaggtg gtcttcgcgg ccttgtgtac acgagcattg ttcgaccact gaaagctccg     960
cttgaagaca caatttcaac cgtccaaatg catgactgga aacttcacgt tttgacgctc    1020
ctattcacaa gcaactttat tggcatcgtt tttgcgcgaa gcatccatta ccaattctac    1080
acttggtact ttcacactgt ctcattctta gtgtacgcca gtggtggaaa cttcgcgttg    1140
tctcttctta tttgcgtttc tctagaagta tgctttaacg tgtatccttc aacagcagaa    1200
tcgagtgcta tcttgcaggc aactcatctt gttttgttat tgagacttgc tacacgaaaa    1260
ccttgcccac ttacagcaca gagcaagcgc cctaaacaag catga                    1305
```

<210> SEQ ID NO 4
<211> LENGTH: 1305
<212> TYPE: DNA
<213> ORGANISM: Artificial Sequence
<220> FEATURE:
<223> OTHER INFORMATION: Synethic
<220> FEATURE:
<221> NAME/KEY: misc_feature
<223> OTHER INFORMATION: SG4EUKT579102, Alg3.2 gene from
Aurantiochytrium

<400> SEQUENCE: 4

```
atgtctttgc gtgcgagtaa ggatgccctc gtacgtcttc gagggccct cgacaatgca      60
agcactcagt ggtggtggtg ggccatggca gccacggcag acttggcact tagcctgctt    120
attgtgaaac tcgtgcctta tacggagatc gactttaaag cgtacatgca agaggttgaa    180
ggccccctat tgcatgatga atgggactat acaaagctca ggggcgacac aggcccgctg    240
gtttatcctg ccggttttgt gtatatttat atgggcatcc gctggctcac tgaagacggc    300
acgaacctgt ggcgaggcca gatacttttt gcaagtctgc atgcaattct tgtttacctt    360
gtacttggat ccatatatta ccagccagat gcatcaaaag atcctcgcag agtgccgttc    420
tgggtaggac ctctagcagt attatcgaga cgtgtgcatt caatctttgt tctgaggctc    480
ttcaacgacg gcattgctat ggtgtttatg tatgcagcag tatatatgta tgtgcggagg    540
cgttggacgc taggtacggc tttcttcagc gcagcactta gcgtgaaaat gaatatactc    600
ctatttgcgc caggattagc cgtgttgatg ctcgaggcta cgggtttggc gtcgagcata    660
ctgcaggcag tgatctgcgt agcatcacag attgccttag cttttgccgtt cctccaagtc    720
aacgcagccg ggtatctaaa tcgggctttt gagctaggtc gtgtctttac gtacaaatgg    780
acagtaaact tcaagtttct cagccctgaa gcttttgtga gtaaggcact tgcccaaggc    840
ctgctgtctg ccactttact tacatgggtc ggctttgggt ctcgccactt tgcttcctct    900
cacacaggtg gtcttcgcgg ccttgtgtac acgagcattg ttcgaccact gaaagctccg    960
cttgaagaca caatttcaac cgtccaaatg catgactgga aacttcacgt tttgacgctc   1020
ctattcacaa gcaactttat tggcatcgtt tttgcgcgaa gcatccatta ccaattctac   1080
acttggtact tcacactgt ctcattctta gtgtacgcca gtggtggaaa cttcgcgttg   1140
tctcttctta tttgcgtttc tctagaagta tgctttaacg tgtatccttc aacagcagaa   1200
tcgagtgcta tcttgcaggc aactcatctt gttttgttat tgagacttgc tacacgaaaa   1260
ccttgcccac ttacagcaca gagcaagcgc cctaaacaag catga                    1305
```

<210> SEQ ID NO 5
<211> LENGTH: 1305
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: SG4EUKT561246, Alg3.3 gene from
Aurantiochytrium

<400> SEQUENCE: 5

```
atgtctttcc gtgcgagtaa ggatgccctc gtacgtcttc gagggccct cgacaatgca      60
agcactcagt ggtggtggtg ggccatggca gccacggcag acttggcact tagcctgctt    120
attgtgaaac tcgtgcctta tacggagatc gactttaaag cgtacatgca agaggttgaa    180
ggccccctac tgcatgatga atgggactat acaaagctca ggggcgacac aggcccgctg    240
gtttatcctg ctggttttgt gtatatttat atgggcatcc gctggctcac tgaagacggc    300
acaaacctgt ggcgaggcca gatacttttt gcaagtctgc atgcaattct tgtttacctt    360
gtacttggat ccatatacta ccagccagat gcatcaaaag atcctcgcag agtgccgttc    420
tgggtaggac ctctagcagt attatcgaga cgtgtgcatt caatctttgt tctgaggctc    480
```

```
ttcaacgacg gcattgctat ggtgtttatg tatgcagcag tatatatgta tgtgcggagg       540
cgttggacgc taggtacggc tttcttcagc gcagcactta gcgtgaaaat gaatatactc       600
ctatttgcgc caggattagc cgtgttgatg ctcgaggcta cgggtttggc gtcgagcata       660
ctgcaggcag tgatctgcgt agcatcacag attgccttag cttcgccgtt cctccaagtc       720
aatgcagcag ggtatctaaa tcgggctttt gagctaggtc gtgtctttac gtacaagtgg       780
acagtaaact tcaagtttct cagccctgaa gcttttgtaa gtaaggcact tgcccaaggc       840
ctgctgtctg ccactttact tacatgggtc ggctttgggt ctcgccattt tgcttcctct       900
cacacaggtg gccttcgcgg ccttgtgtac acgagcattg ttcgaccact gaaagctccg       960
cttgaagaca caatttcaac cgtccaaatg catgactgga aacttcacgt tttgacgctc      1020
ctattcacaa gcaactttat tggcatcgtt tttgcgcgaa gcatccatta ccaattctac      1080
acttggtact ttcacactgt ctcattctta gtgtacgcca gtggtggaaa cttcgcgttg      1140
tctcttctta tttgcgtttc tctagaagta tgctttaacg tgtatccttc aacagcagaa      1200
tcgagtgcta tcttgcaggc aactcatctt gttttgttat tgagacttgc tacacgaaaa      1260
ccttgcccac ttacagcaca gagcaagcgc cctaaacaag catga                      1305
```